(12) United States Patent
Jang et al.

(10) Patent No.: US 8,932,861 B2
(45) Date of Patent: *Jan. 13, 2015

(54) TRANSFORMATION VECTOR COMPRISING TRANSPOSON, MICROORGANISMS TRANSFORMED WITH THE VECTOR, AND METHOD FOR PRODUCING L-LYSINE USING THE MICROORGANISM

(71) Applicant: CJ Cheiljedang Corporation, Seoul (KR)

(72) Inventors: Jae-Woo Jang, Gyeonggi-do (KR); Sang-Jo Lim, Incheon (KR); Jong-Soo Choi, Seoul (KR); Chul-Ha Kim, Seoul (KR); Jun-Ok Moon, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/683,096

(22) Filed: Nov. 21, 2012

(65) Prior Publication Data

US 2013/0157370 A1 Jun. 20, 2013

Related U.S. Application Data

(63) Continuation-in-part of application No. 12/867,649, filed as application No. PCT/KR2009/001845 on Apr. 10, 2009, now Pat. No. 8,323,933.

(30) Foreign Application Priority Data

Apr. 10, 2008 (KR) .................. 10-2008-0033054

(51) Int. Cl.
| | |
|---|---|
| C12N 9/00 | (2006.01) |
| C12N 1/20 | (2006.01) |
| C12N 15/00 | (2006.01) |
| C07H 21/04 | (2006.01) |
| C12N 15/77 | (2006.01) |
| C12N 9/22 | (2006.01) |
| C12N 15/90 | (2006.01) |
| C12P 13/08 | (2006.01) |

(52) U.S. Cl.
CPC ...... *C12N 15/77* (2013.01); *C12N 9/22* (2013.01); *C12N 15/902* (2013.01); *C12P 13/08* (2013.01)
USPC ..... 435/471; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,457,040 A | 10/1995 | Jarry et al. | |
| 5,633,154 A | 5/1997 | Schaefer et al. | |
| 5,804,414 A | 9/1998 | Moriya | |
| 6,200,785 B1 | 3/2001 | Kreutzer et al. | |
| 6,221,636 B1 | 4/2001 | Hayakawa et al. | |
| 6,740,742 B2 | 5/2004 | Mockel et al. | |
| 6,746,855 B2 | 6/2004 | Kreutzer et al. | |
| 6,861,246 B2 | 3/2005 | Kreutzer et al. | |
| 6,872,553 B2 | 3/2005 | Eikmanns et al. | |
| 6,913,909 B2 | 7/2005 | Ziegler et al. | |
| 6,962,989 B1 | 11/2005 | Pompejus et al. | |
| 7,160,711 B2 | 1/2007 | Bathe et al. | |
| 8,048,650 B2 | 11/2011 | Koo et al. | |
| 8,058,036 B2 | 11/2011 | Koo et al. | |
| 8,323,933 B2 * | 12/2012 | Jang et al. ..................... 435/115 |
| 2002/0055153 A1 | 5/2002 | Kreutzer et al. | |
| 2002/0197605 A1 | 12/2002 | Nakagawa | |
| 2002/1962674 | 12/2002 | Hermann et al. | |
| 2003/0055232 A1 | 3/2003 | Li et al. | |
| 2005/0153402 A1 | 7/2005 | Pompejus et al. | |
| 2005/0255568 A1 | 11/2005 | Bailey et al. | |
| 2006/0084152 A1 | 4/2006 | Pompejus et al. | |
| 2008/0293100 A1 | 11/2008 | Wendisch et al. | |
| 2010/0015673 A1 | 1/2010 | Koo et al. | |
| 2010/0028957 A1 | 2/2010 | Koo et al. | |
| 2010/0129884 A1 | 5/2010 | Cho et al. | |

FOREIGN PATENT DOCUMENTS

| | | |
|---|---|---|
| CN | 1187540 A | 7/1998 |
| DE | 101 10 760 A1 | 8/2002 |
| EP | 0733710 | 9/1996 |
| EP | 0854189 | 7/1998 |
| EP | 1715055 | 10/2006 |
| JP | 62-079788 | 4/1987 |
| JP | H06-046867 | 2/1994 |
| JP | Hei 7-121228 | 12/1995 |
| JP | 09-070291 | 3/1997 |
| JP | 10-215883 | 8/1998 |
| JP | 2001-037495 | 2/2001 |
| JP | 2002-508921 | 3/2002 |
| JP | 2003-503006 | 1/2003 |
| JP | 2006-512922 | 4/2006 |
| KR | 10-0313134 | 10/2001 |
| KR | 1020050065712 | 6/2005 |
| KR | 1020060068505 | 6/2006 |

(Continued)

OTHER PUBLICATIONS

Accession AX121271, May 2001.
Accession AXBX248360, Nov. 2006.
Beijer et al. (1992) FEMS Microbiology Letters 100:217-220, "Utilisation of glycerol and glycerol 3-phosphate is differently affected by the• phosphotransferase system in *Bacillus subtilis*".
Beijer et al. (1993) Journal of General Microbiology, 139(2):349-359, "The glpP and glpF genes of the glycerol regulon in *Bacillus subtilis*".
Biebl (1998) Appl Microbiol Biotechnol. 50:24-29, "Fermentation of glycerol to 1,3-propanediol and 2,3-butanediol by Klebsiella pneumonia".
Cerdeno-Tarraga et al. (2003) Nucleic Acids Research 31(22):6516-6523 , "The complete genome sequence and analysis of *Corynebacterium diphtheriae* NCTC13129".
Contador et al. (2009) "Ensemble modeling for strain development of l-lysine-producing *Escherichia coli*," Metabolic Engineering, pp. 221-233, vol. 11, No. 4-5, Academic Press.
Database UnitProt [Online] Jul. 5, 2004, "SubName: Full=Putative uncharacterized protein".

(Continued)

*Primary Examiner* — Christian Fronda
(74) *Attorney, Agent, or Firm* — Sawnson & Bratschun, L.L.C.

(57) ABSTRACT

The present invention relates to a transformation vector comprising the partial fragments of a gene encoding transposase, a microorganism transformed with the vector, and a method of producing lysine using the microorganism.

4 Claims, 10 Drawing Sheets

(56) References Cited

FOREIGN PATENT DOCUMENTS

| KR | 10-2008-025355 | 3/2008 |
|---|---|---|
| WO | WO 92/02627 | 2/1992 |
| WO | WO 02/053707 | 7/2002 |
| WO | WO 2005/121349 | 12/2005 |
| WO | WO 2006/065095 | 6/2006 |
| WO | WO 2006/071099 | 7/2006 |
| WO | WO 2007/039532 | 4/2007 |
| WO | WO 2008/033001 | 3/2008 |

OTHER PUBLICATIONS

Doleyres et al. (2005) Appl Microbiol Biotechnol. 68:467-474, "Production of 3-hydroxypropionaldehyde using a two-step process with *Lactobacillus reuteri*".

Eggeling (1994) Amino Acids 6:261-272, "Biology of L-lysine overproduction by *Corynebacterium glutamicum*".

European Search Report issued Dec. 30, 2009 in PCT/KR2007/006935.

Extended European Search Report dated Jan. 5, 2010, for European Patent Application No. 07808268.

GenBank Accession No. BA000036.3, (2003).

González-Pajuelo et al. (2004) J Ind Microbiol Biotechnol. 31:442-446, "Production of 1,3-propanediol by *Clostridium butyricum* VPI 3266 using a synthetic medium and raw glycerol".

Hayashi et al. (2006) Appl Microbiol Biotechnol 72:783-789, "A *leuC* mutation leading to increased L-lysine production and *rel*-independent global expression changes in *Corynebacterium glutamicum*".

Hayes (2003) Annu. Rev. Genet. 37:3-29, "Transposon-Based Strategies for Microbial Functional Genomics and Proteomics".

Heller et al. (1980) Journal of Bacteriology 144(1):274-278, "Substrate Specificity and Transport Properties of the Glycerol Facilitator of *Escherichia coli*".

Himmi et al. (2000) Appl Microbiol Biotechnol 53:435-440, "Propionic acid fermentation of glycerol and glucose by *Propionbacterium acidipropionici* and *Propionibacterium freudenreichii* ssp. shermanii".

Ikeda et al. (2003) App. Microbiol. and Biotechnol. 62(2-3, 1): 99-109, "The *Corynebacterium glutamicum* genome: Features and impacts on biotechnological processes".

International Search Report dated Jan. 2, 2008, for PCT International Patent Application No. PCT/KR2007/004478.

International Search Report and Written Opinion dated May 16, 2008 from PCT/KR2008/000391.

International Search Report issued in PCT/KR2009/001845 mailed Nov. 27, 2009.

Ito et al. (2005) Journal of Bioscience and Bioengineering 100(3):260-265, "Hydrogen and Ethanol Production from Glycerol-Containing Wastes Discharged after Biodiesel Manufacturing Process".

Kawaguchi et al. (2006) Applied and Environmental Microbiology 72(5):3418-3428, "Engineering of a Xylose Metabolic Pathway in *Corynebacterium glutamicum*".

Koffas et al. (2002) "Effect of pyruvate carboxylase overexpression on the physiology of *Corynebacterium glutamicum*," Applied and Environmental Microbiology, Nov. 2002, pp. 5422-5428, vol. 68, No. 11.

Liebl (1991) "Transfer of Brevibacterium divaricatum DSM 20297T, "Brevibacterium flavum" DSM 20411, "Brevibacterium lactofermenturn" DSM 20412 and DSM 1412, and *Corynebacteriumlilium* DSM 20137T to *Corynebacteriurn glutamicum* and Their Distinction by rRNA Gene Restriction Patterns" International Journal of Systematic Bacteriology, vol. 41, pp. 255-260.

Lin et al. (1976) Ann. Rev. Microbiol. 30:535-578, "Glycerol Dissimilation and its Regulation in Bacteria".

Menzel (1997) Enzyme and Microbial Technology 20:82-86, "High Concentration and Productivity of 1,3-propanediol from continuous fermentation of glycerol by *Klebsiella pneumoniae*".

Mitsuhashi et al. (2006) Biosci., Biotechnol., and Biochem. 70(11): 2803-2806, "Disruption of malate:quinone oxidoreductase increases L-lysine production by *Corynebacterium glutamicum*".

Moon et al. (2005) FEMS Microbiology Letters, "Analyses of enzyme II gene mutants for sugar transport and heterologous express of fructokinase gene in *Corynebacterium glutamicum* ATCC 13032," vo. 244, p. 259-266.

Mormann (2006) BMC Genomics, 7:205, doi:10.1186/1471-2164-205, "Random mutagenesis in *Corynebacterium glutamicum* ATCC 13032 using an IS6100-based transposon vector identified the last unknown gene in the histidine biosynthesis pathway".

Nishise et al. (1985) Agri. Biol. Chem. 49(3):629-636, "Glycerol Dehydrogenase and Glycerol Dissimilation in *Cellulomonas* sp. NT3060t".

Office Action issued Jan. 7, 2011 in U.S. Appl. No. 12/518,572.
Office Action issued Jan. 12, 2011 in U.S. Appl. No. 12/518,578.
Office Action issued Jul. 6, 2011 in U.S. Appl. No. 12/518,572.
Office Action issued Jul. 11, 2011 in U.S. Appl. No. 12/518,578.

Parche et al. (2001) J. Mol. Microbiol. Biotechnol. 3(3):415-422, "*Corynebacterium diphtheriae*: a PTS View to the Genome".

Paulsen et al. (2000) Microbiology146:2343-2344, "Functional genomic studies of dihydroxyacetone utilization in *Escherichia coli*".

PCT International Preliminary Report on Patentability issued Oct. 12, 2010 and Written Opinion for PCT/KR2009/001845.

Peters-Wendisch et al. (2005) Applied and Environmental Microbiology, 71(11):7139-7144, "Metabolic Engineering of *Corynebacterium glutamicum* for L-Serine Production".

Tangney et al. (2000) J. Mol. Microbiol. Biotechnol. 2(1):71-80, Analysis of a Catabolic Operon for Sucrose Transport and Metabolism in *Clostridium acetobutylicum* ATCC 824.

Talarico et al. (1988) Antimicrobial Agents and Chemotherapy 32(12):1854-1858, "Production and Isolation of Reuterin, a Growth Inhibitor Produced by *Lactobacillus reuteri*".

Tsuge et al. (2005) Microbiology 151:501-508, "A New Insertion Sequence, ISI4999, from *Corynebacterium glutamicum*".

Tzvetkov et al. (2003) Microbiology 149(7):1659-1673, "Genetic dissection of trehalose biosynthesis in *Corynebacterium glutamicum*: Inactivation of trehalose production leads to impaired growth and altered cell wall lipid composition".

Vertes (1994) "Transposon Mutagenesis of Coryneform Bacteria" Mol.Gen.Genet.,vol. 245, pp. 397-405.

Voegele (1993) Journal of Bacteriology, 175(4):1087-1094, "Glycerol Kinase of *Escherichia coli* Is Activated by Interaction with the Glycerol Facilitator".

Wang et al. (2001) Biotechnology Advances 19:201-223, "Glycerol production by microbial fermentation: A review".

\* cited by examiner

SEQUENCE LISTING

<160> NUMBER OF SEQ ID NOS: 38

<210> SEQ ID NO 1
<211> LENGTH: 510
<212> TYPE: DNA
<213> ORGANISM: Corynebacterium glutamicum

<400> SEQUENCE: 1

```
gcagacgcac tcgactacac ctccacctgc ccagaatgct cccaacctgg ggtgtttcgt      60
catcacaccc accggatgct cattgattta cccatcgtcg ggtttcccac caaactgttt     120
atccgtctac ctcgctaccg ctgcaccaac cccacatgta agcaaaagta tttccaagca     180
gaactaagct gcgctgacca cggtaaaaag gtcacccacc gggtcacccg ctggatttta     240
caacgccttg ctattgaccg gatgagtgtt cacgcaaccg cgaaagcact tgggctaggg     300
tgggatttaa cctgccaact agccctcgat atgtgccgtg agctggtcta taacgatcct     360
caccatcttg atggagtgta tgtcattggg gtggatgagc ataagtggtc acataatagg     420
gctaagcatg gtgatgggtt tgtcaccgtg attgtcgata tgaccgggca tcggtatgac     480
tcacggtgtc ctgcccggtt attagatgtc                                      510
```

<210> SEQ ID NO 2
<211> LENGTH: 479
<212> TYPE: DNA
<213> ORGANISM: Corynebacterium glutamicum

<400> SEQUENCE: 2

```
aactcattcc ttctgctcgt cgcgtgatgg atccattcca tgttgtgcgg cttgctggtg      60
acaagctcac cgcctgccgg caacgcctcc agcgggagaa ataccagcgt cgtggtttaa     120
gccaggatcc gttgtataaa aaccggaaga ccttgttgac cacgcacaag tggttgagtc     180
ctcgtcagca agaaagcttg gagcagttgt gggcgtatga caaagactac ggggcgttaa     240
agcttgcgtg gcttgcgtat caggcgatta ttgattgtta tcagatgggt aataagcgtg     300
aagcgaagaa gaaaatgcgg accattattg atcagcttcg ggtgttgaag gggccgaata     360
aggaactcgc gcagttgggt cgtagtttgt ttaaacgact tggtgatgtg ttggcgtatt     420
tcgatgttgg tgtctccaac ggtccggtcg aagcgatcaa cggacggttg gagcatttg      479
```

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3

```
atcctctaga gtcgaccatc gctgacacca tctgcc                                36
```

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
gggcccacta gtctcgagtt caccgcggga gccaagcc                      38

<210> SEQ ID NO 5
<211> LENGTH: 37
<212> TYPE: DNA
<213> ORGANISM: Artificial Sequence
<220> FEATURE:
<223> OTHER INFORMATION: Primer

<400> SEQUENCE: 5
ctcgagacta gtgggccctg gattccaagg ctacgcc                       37

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
atgcctgcag gtcgaccctg aatggataag gcaccg                        36

<210> SEQ ID NO 7
<211> LENGTH: 37
<212> TYPE: DNA
<213> ORGANISM: Artificial Sequence
<220> FEATURE:
<223> OTHER INFORMATION: Primer

<400> SEQUENCE: 7
tgtcgggccc actagttccc agggtagttg actaaag                       37

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gaatgagttc ctcgagtatc aacgcgtcgg taga                          34

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gctaccgctg caccaacccc                                          20

<210> SEQ ID NO 10
<211> LENGTH: 30
<212> TYPE: DNA
<213> ORGANISM: Artificial Sequence
<220> FEATURE:
<223> OTHER INFORMATION: Primer

```
<400> SEQUENCE: 10
ttcacgccga attcgacaag gcaatcaccg                                      30

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
tgtcgggccc actagttcat tggcgtttcc ggatcc                               36

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
gaatgagttc ctcgagacaa gcgccaagga actacc                               36

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
acaagcgcca aggaactacc                                                 20

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14
tgtcgggccc actagtcata tgaataatgt tttatgtatg ggagaa                    46

<210> SEQ ID NO 15
<211> LENGTH: 46
<212> TYPE: DNA
<213> ORGANISM: Artificial Sequence
<220> FEATURE:
<223> OTHER INFORMATION: Primer

<400> SEQUENCE: 15
gaatgagttc ctcgagatac cattctagag ggcttaaagc taccgg                    46

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
ataccattct agagggctta aagctaccgg                                      30

<210> SEQ ID NO 17
<211> LENGTH: 1266
```

<212> TYPE: DNA
<213> ORGANISM: Corynebacterium glutamicum

<400> SEQUENCE: 17

```
gtggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttcacggg ctctcaggct      300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc      780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 18
<211> LENGTH: 1035
<212> TYPE: DNA
<213> ORGANISM: Corynebacterium glutamicum

<400> SEQUENCE: 18

```
atgaccacca tcgcagttgt tggtgcaacc ggccaggtcg ccaggttat gcgcacccctt       60
ttggaagagc gcaatttccc agctgacact gttcgttct ttgcttcccc acgttccgca      120
ggccgtaaga ttgaattccg tggcacggaa atcgaggtag aagacattac tcaggcaacc     180
gaggagtccc tcaaggacat cgacgttgcg ttgttctccg ctggaggcac cgcttccaag     240
cagtacgctc cactgttcgc tgctgcaggc gcgactgttg tggataactc ttctgcttgg     300
cgcaaggacg acgaggttcc actaatcgtc tctgaggtga acccttccga caaggattcc     360
ctggtcaagg gcattattgc gaaccctaac tgcaccacca tggctgcgat gccagtgctg     420
aagccacttc acgatgccgc tggtcttgta aagcttcacg tttcctctta ccaggctgtt     480
tccggttctg gtcttgcagg tgtggaaacc ttggcaaagc aggttgctgc agttggagac     540
cacaacgttg agttcgtcca tgatggacag gctgctgacg caggcgatgt cggaccttat     600
gtttcaccaa tcgcttacaa cgtgctgcca ttcgccggaa acctcgtcga tgacggcacc     660
```

```
ttcgaaaccg atgaagagca gaagctgcgc aacgaatccc gcaagattct cggtctccca      720
gacctcaagg tctcaggcac ctgcgtccgc gtgccggttt tcaccggcca cacgctgacc      780
attcacgccg aattcgacaa ggcaatcacc gtggaccagg cgcaggagat cttgggtgcc      840
gcttcaggcg tcaagcttgt cgacgtccca accccacttg cagctgccgg cattgacgaa      900
tccctcgttg gacgcatccg tcaggactcc actgtcgacg ataaccgcgg tctggttctc      960
gtcgtatctg cgacaaccct ccgcaagggt gctgcgctaa acaccatcca gatcgctgag      1020
ctgctggtta agtaa                                                       1035
```

<210> SEQ ID NO 19
<211> LENGTH: 906
<212> TYPE: DNA
<213> ORGANISM: Corynebacterium glutamicum

<400> SEQUENCE: 19

```
atgagcacag gtttaacagc taagaccgga gtagagcact tcggcaccgt tggagtagca      60
atggttactc cattcacgga atccggagac atcgatatcg ctgctggccg cgaagtcgcg      120
gcttatttgg ttgataaggg cttggattct ttggttctcg cgggcaccac tggtgaatcc      180
ccaacgacaa ccgccgctga aaaactagaa ctgctcaagg ccgttcgtga ggaagttggg      240
gatcgggcga agctcatcgc cggtgtcgga accaacaaca cgcggacatc tgtggaactt      300
gcggaagctg ctgcttctgc tggcgcagac ggccttttag ttgtaactcc ttattactcc      360
aagccgagcc aagagggatt gctggcgcac ttcggtgcaa ttgctgcagc aacagaggtt      420
ccaatttgtc tctatgacat tcctggtcgg tcaggtattc caattgagtc tgataccatg      480
agacgcctga gtgaattacc tacgattttg gcggtcaagg acgccaaggg tgacctcgtt      540
gcagccacgt cattgatcaa agaaacggga cttgcctggt attcaggcga tgacccacta      600
aaccttgttt ggcttgcttt gggcggatca ggtttcattt ccgtaattgg acatgcagcc      660
cccacagcat tacgtgagtt gtacacaagc ttcgaggaag cgacctcgt  ccgtgcgcgg      720
gaaatcaacg ccaaactatc accgctggta gctgcccaag gtcgcttggg tggagtcagc      780
ttggcaaaaag ctgctctgcg tctgcagggc atcaacgtag agatcctcg acttccaatt      840
atggctccaa atgagcagga acttgaggct ctccgagaag acatgaaaaa agctggagtt      900
ctataa                                                                906
```

<210> SEQ ID NO 20
<211> LENGTH: 780
<212> TYPE: DNA
<213> ORGANISM: Corynebacterium glutamicum

<400> SEQUENCE: 20

```
atgggaatca aggttggcgt tctcggagcc aaaggccgtg ttggtcaaac tattgtggca      60
gcagtcaatg agtccgacga tctggagctt gttgcagaga tcggcgtcga cgatgatttg      120
agccttctgg tagacaacgg cgctgaagtt gtcgttgact tcaccactcc taacgctgtg      180
atgggcaacc tggagttctg catcaacaac ggcatttctg cggttgttgg aaccacgggc      240
ttcgatgatg ctcgttttga gcaggttcgc gactggcttg aaggaaaaga caatgtcggt      300
gttctgatcg cacctaactt tgctatctct gcggtgttga ccatggtctt ttccaagcag      360
gctgcccgct tcttcgaatc agctgaagtt attgagctgc accacccaa caagctggat      420
gcaccttcag gcaccgcgat ccacactgct cagggcattg ctgcggcacg caaagaagca      480
ggcatggacg cacagccaga tgcgaccgag caggcacttg agggttcccg tggcgcaagc      540
```

```
gtagatggaa tcccggttca tgcagtccgc atgtccggca tggttgctca cgagcaagtt    600
atctttggca cccagggtca gaccttgacc atcaagcagg actcctatga tcgcaactca    660
tttgcaccag gtgtcttggt gggtgtgcgc aacattgcac agcacccagg cctagtcgta    720
ggacttgagc attacctagg cctgtaaagg ctcatttcag cagcgggtgg aattttttaa    780
```

<210> SEQ ID NO 21
<211> LENGTH: 949
<212> TYPE: DNA
<213> ORGANISM: Corynebacterium glutamicum

<400> SEQUENCE: 21

```
atgaataatg ttttatgtat aggagaactt ttaatcgatt ttatatgttc tgatatagat     60
acaactcttt ctaaaggaga aaactttaag aagaaggcag gaggggcacc tgcaaatgta    120
acggcagcaa tttcaaagct tggaggaagt gcgtcttttt taggtaaggt tgggaatgat    180 cccttttggac attttttgaa agagacttta gatgaagtta aggtagatac atcaatgctt    240
attatggata caactcaag tactactctt catttgtgtc acttcaggca aatggtgaaa    300
gagattttgt ctttaatagg ggagcagatg gtcttttaag atatgatgaa ataaatttag    360
ataaagttta ctcaaataaa ataattcact ttggttccgc aactgcttta ttaggtggag    420
aaatgacaga cacttactta aagataatgg aggaagcgaa gaaaggggga ataattatat    480
cctttgatcc aaactacaga gataatcttt gggaaaacag aacagaagag tttatagcta    540
tttcacgtag tgcattgaac ttgctgattt tgtgaaatta agtgacgagg aattaaaaat    600
tatatctgga gagaaaaata taaaaaatgg agtaaagctt ttagcttcaa ataacaaggt    660
tattgctgta actttaggaa aagagggtac tatgatttca aatggagaag aagttgaaat    720
catagagagt ataaaaataa aatctataga ttctaccgga gcaggagatg catttgtggg    780
agcatttctt tataaaattgt cagaggcatt agaggcaaga gatattttaa gtgactttaa    840
taaaatcaag gaaaatgttc gctttgcaaa taaggttggt gcaattgtgt gtacaaagct    900
tggtgctata agttctcttc ctagtttaag tgaagttgaa ggtgattag                949
```

<210> SEQ ID NO 22
<211> LENGTH: 1311
<212> TYPE: DNA
<213> ORGANISM: Corynebacterium glutamicum

<400> SEQUENCE: 22

```
atgaagtcta ccggcaacat catcgctgac accatctgcc gcactgcgga actaggactc     60
accatcaccg gcgcttccga tgcaggtgat tacaccctga tcgaagcaga cgcactcgac    120
tacacctcca cctgcccaga atgctcccaa cctggggtgt tcgtcatca cccccaccgg    180 atgctcattg attacccat cgtcgggttt cccaccaaac tgtttatccg tctacctcgc    240
taccgctgca ccaaccccac atgtaagcaa aagtatttcc aagcagaact aagctgcgct    300
gaccacggta aaaaggtcac ccaccgggtc acccgctgga ttttacaacg ccttgctatt    360
gaccggatga gtgttcacgc aaccgcgaaa gcacttgggc tagggtggga tttaacctgc    420
caactagccc tcgatatgtg ccgtgagctg gtctataacg atcctcacca tcttgatgga    480
gtgtatgtca ttggggtgga tgagcataag tggtcacata atagggctaa gcatggtgat    540
gggtttgtca ccgtgattgt cgatatgacc gggcatcggt atgactcacg gtgtcctgcc    600
cggttattag atgtcgtccc aggtcgtagt gctgatgctt tacggtcctg gcttggctcc    660
```

-continued

| | |
|---|---|
| cgcggtgaac agttccgcaa tcagatacgg atcgtgtcca tggatggatt ccaaggctac | 720 |
| gccacagcaa gtaaagaact cattccttct gctcgtcgcg tgatggatcc attccatgtt | 780 |
| gtgcggcttg ctggtgacaa gctcaccgcc tgccggcaac gcctccagcg ggagaaatac | 840 |
| cagcgtcgtg gtttaagcca ggatccgttg tataaaaacc ggaagacctt gttgaccacg | 900 |
| cacaagtggt tgagtcctcg tcagcaagaa agcttggagc agttgtgggc gtatgacaaa | 960 |
| gactacgggg cgttaaagct tgcgtggctt gcgtatcagg cgattattga ttgttatcag | 1020 |
| atgggtaata agcgtgaagc gaagaagaaa atgcggacca ttattgatca gcttcgggtg | 1080 |
| ttgaaggggc cgaataagga actcgcgcag ttgggtcgta gtttgtttaa acgacttggt | 1140 |
| gatgtgttgg cgtatttcga tgttggtgtc tccaacggtc cggtcgaagc gatcaacgga | 1200 |
| cggttggagc atttgcgtgg gattgctcta ggtttccgta atttgaacca ctacattctg | 1260 |
| cggtgcctta tccattcagg gcagttggtc cataagatca atgcactcta a | 1311 |

<210> SEQ ID NO 23
<211> LENGTH: 325
<212> TYPE: DNA
<213> ORGANISM: Corynebacterium glutamicum

<400> SEQUENCE: 23

| | |
|---|---|
| atagggctaa gcatggtgat gggtttgtca ccgtgattgt cgatatgacc gggcatcggt | 60 |
| atgactcacg gtgtcctgcc cggttattag atgtcgtccc aggtcgtagt gctgatgctt | 120 |
| tacggtcctg gcttggctcc cgcggtgaac agttccgcaa tcagatacgg atcgtgtcca | 180 |
| tggatggatt ccaaggctac gccacagcaa gtaaagaact cattccttct gctcgtcgcg | 240 |
| tgatggatcc attccatgtt gtgcggcttg ctggtgacaa gctcaccgcc tgccggcaac | 300 |
| gcctccagcg ggagaaatac cagcg | 325 |

<210> SEQ ID NO 24
<211> LENGTH: 299
<212> TYPE: DNA
<213> ORGANISM: Corynebacterium glutamicum

<400> SEQUENCE: 24

| | |
|---|---|
| gattattgat tgttatcaga tgggtaataa gcgtgaagcg aagaagaaaa tgcggaccat | 60 |
| tattgatcag cttcgggtgt tgaaggggcc gaataaggaa ctcgcgcagt tgggtcgtag | 120 |
| tttgtttaaa cgacttggtg atgtgttggc gtatttcgat gttggtgtct ccaacggtcc | 180 |
| ggtcgaagcg atcaacggac ggttggagca tttgcgtggg attgctctag gtttccgtaa | 240 |
| tttgaaccac tacattctgc ggtgccttat ccattcaggg cagttggtcc ataagatca | 299 |

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25

| | |
|---|---|
| atcctctaga gtcgacatag ggctaagcat ggtgat | 36 |

<210> SEQ ID NO 26
<211> LENGTH: 39
<212> TYPE: DNA
<213> ORGANISM: Artificial Sequence
<220> FEATURE:
<223> OTHER INFORMATION: Primer -continued

```
<400> SEQUENCE: 26
gggcccacta gtctcgagcg ctggtatttc tcccgctgg                                 39

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
ctcgagacta gtgggcccga ttattgattg ttatcagat                                 39

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
atgcctgcag gtcgactgat cttatggacc aactgccc                                  38

<210> SEQ ID NO 29
<211> LENGTH: 1611
<212> TYPE: DNA
<213> ORGANISM: Artificial Sequence
<220> FEATURE:
<223> OTHER INFORMATION: Primer

<400> SEQUENCE: 29
atgcaccacg agcaacccga agggtgcgaa gtgggcattc gtagaacaat cccagaggaa          60
agccgtacgg ctttcctcga catgatcaat caaggtatgt caggtcttgc tgcgtctaca         120
gcggtcgggg tcagtgaatt caccgggcga agtgggcga aggccgccgg ggtgaaactg          180
acccgcggcc cgcgaggtgg caatgctttt gacaccgccg agaaacttga gattgcagcc         240
agcatgctag agaaaggatg cctaccccga gaaatcggcg agtatgtcgg catgactcgg         300
gccaatatat ccctatggcg caaacaaggc ccagacaagc ttcgccaacg cgcagccacc         360
ttgcgcaccg gcaagcgagc agctgaattc atccacgccc cggtgatggg cccttattat         420
gggccacgca cactccatca agtgttgcgt gaggactaca caacactgtt tgacgagtta         480
tctgcgttgg ggttgccagc acaggtgtgt ggggccttac ttcatcttgc tccaccacca         540
tcattacgct tttcttatat gtcgtgtgta gtgccgttat ttgctgatga atcaaagtc          600 gtaggacaag gcacacgatt atcgttagaa gagaaaatga tgatccaacg tttccatgac         660 accgggtca gtgcagcaga aatcggtcga cgcctgggtc ggtgtcggca acaatttcc          720 agggaacttc gacgtggtca agatgatgat ggacgttatc gtgcacgcga ctcctatgaa         780
ggtgcgatca ggaaactagc gcgtccgaaa acaccgaaac ttgatgccaa tcgtaggctt         840
cgggctgtgg tggtcgaggc gttgaataat aaattatctc cggagcagat ttctggtctt         900
ttagccaccg agcatgctaa cgatagctct atgcagatta gtcatgaaac tatttaccag         960
gcgttatatg ttcaaggtaa aggggcgttg cgtgatgaat tgaaggtgga gaaatttctt        1020
cgtaccggtc ggaagggacg taaaccgcag tcgaagttgc catcgagagg taagccgtgg        1080
gtggagggtg cgttgattag tcaacgccca gcagaagttg ctgatcgtgc tgtgcctggg        1140
cactgggagg gcgatttagt aattggtggt gaaaaccaag cgacagcgtt ggtgacgttg        1200
```

```
gtggagcgca cgagccggtt gacgttgatt aagcggttgg gggttaatca tgaggcgtcg    1260
actgtgacgg atgcgttggt ggagatgatg ggtgatttgc cgcaggcgtt gcgtcggagt    1320
ttgacgtggg atcagggtgt ggagatggca gagcatgcgc ggtttagcgt ggtgaccaag    1380
tgtccggtgt ttttctgtga tcctcattcg ccgtggcagc gtgggtcgaa tgagaatacg    1440
aatggattgg tcagggattt ttcccgaag ggcactaatt ttgctaaagt aagtgacgaa    1500
gaagttcagc gggcacagga tctgctgaat taccggccgc ggaaaatgca tggttttaaa    1560
agcgcgacgc aggtatatga aaaaatcgta gttggtgcat ccaccgattg a             1611
```

<210> SEQ ID NO 30
<211> LENGTH: 36
<212> TYPE: DNA
<213> ORGANISM: Artificial Sequence
<220> FEATURE:
<223> OTHER INFORMATION: Primer
<400> SEQUENCE: 30

```
atcctctaga gtcgaccacg cacactccat caagtg                               36
```

<210> SEQ ID NO 31
<211> LENGTH: 40
<212> TYPE: DNA
<213> ORGANISM: Artificial Sequence
<220> FEATURE:
<223> OTHER INFORMATION: Primer
<400> SEQUENCE: 31

```
tctcgagact agtgggccgc atagagctat cgttagcatg                           40
```

<210> SEQ ID NO 32
<211> LENGTH: 45
<212> TYPE: DNA
<213> ORGANISM: Artificial Sequence
<220> FEATURE:
<223> OTHER INFORMATION: Primer
<400> SEQUENCE: 32

```
cggcccacta gtctcgagag aggtaagccg tgggtggagg gtgcg                     45
```

<210> SEQ ID NO 33
<211> LENGTH: 37
<212> TYPE: DNA
<213> ORGANISM: Artificial Sequence
<220> FEATURE:
<223> OTHER INFORMATION: Primer
<400> SEQUENCE: 33

```
atgcctgcag gtcgacgtaa ttcagcagat cctgtgc                              37
```

<210> SEQ ID NO 34
<211> LENGTH: 510
<212> TYPE: DNA
<213> ORGANISM: Artificial Sequence
<220> FEATURE:
<223> OTHER INFORMATION: Primer
<400> SEQUENCE: 34

```
cacgcacact ccatcaagtg ttgcgtgagg actacacaac actgtttgac gagttatctg    60
cgttggggtt gccagcacag gtgtgtgggg ccttacttca tcttgctcca ccaccatcat    120
tacgcttttc ttatatgtcg tgtgtagtgc cgttatttgc tgatgaaatc aaagtcgtag    180
gacaaggcac acgattatcg ttagaagaga aaatgatgat ccaacgtttc catgacaccg    240
```

-continued

```
gggtcagtgc agcagaaatc ggtcgacgcc tgggtcggtg tcggcaaaca atttccaggg    300
aacttcgacg tggtcaagat gatgatggac gttatcgtgc acgcgactcc tatgaaggtg    360
cgatcaggaa actagcgcgt ccgaaaacac cgaaacttga tgccaatcgt aggcttcggg    420
ctgtggtggt cgaggcgttg aataataaat tatctccgga gcagatttct ggtcttttag    480
ccaccgagca tgctaacgat agctctatgc                                     510
```

<210> SEQ ID NO 35
<211> LENGTH: 468
<212> TYPE: DNA
<213> ORGANISM: Artificial Sequence
<220> FEATURE:
<223> OTHER INFORMATION: Primer

<400> SEQUENCE: 35

```
agaggtaagc cgtgggtgga gggtgcgttg attagtcaac gcccagcaga agttgctgat     60
cgtgctgtgc ctgggcactg ggagggcgat ttagtaattg gtggtgaaaa ccaagcgaca    120
gcgttggtga cgttggtgga gcgcacgagc cggttgacgt tgattaagcg gttggggtt     180 aatcatgagg cgtcgactgt gacggatgcg ttggtggaga tgatgggtga tttgccgcag    240
gcgttgcgtc ggagtttgac gtgggatcag ggtgtggaga tggcagagca tgcgcggttt    300
agcgtggtga ccaagtgtcc ggtgttttc tgtgatcctc attcgccgtg gcagcgtggg    360
tcgaatgaga atacgaatgg attggtcagg gattttttcc cgaagggcac taattttgct    420
aaagtaagtg acgaagaagt tcagcgggca caggatctgc tgaattac                 468
```

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36

```
cacgcacact ccatcaagtg                                                 20
```

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37

```
atgagtaaag gagaagaact ttt                                             23
```

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38

```
ttatttgtag agctcatcca tgcc                                            24
```

US 8,932,861 B2

TRANSFORMATION VECTOR COMPRISING TRANSPOSON, MICROORGANISMS TRANSFORMED WITH THE VECTOR, AND METHOD FOR PRODUCING L-LYSINE USING THE MICROORGANISM

RELATED APPLICATIONS

The present application is a continuation-in-part application of U.S. patent application Ser. No. 12/867,649 filed on Aug. 13, 2010, which is a national phase entry under 35 U.S.C. 371 of International Application No. PCT/KR2009/001845 filed on Apr. 10, 2009, which claims the benefit of Korean Patent Application No. 10-2008-0033054 filed on Apr. 10, 2008. The disclosures of said applications are incorporated by reference herein.

Incorporated by reference herein in its entirety is the Sequence Listing entitled "SEQUENCE_LST", created Nov. 20, 2012, size of 21 kilobytes.

BACKGROUND OF THE INVENTION

1. Field of the Invention

The present invention relates to a transformation vector comprising the partial fragments of a gene encoding transposase, a microorganism transformed with the vector, and a method of producing lysine using the microorganism.

2. Description of the Prior Art

Corynebacterium, especially Corynebacterium glutamicum, is a Gram-positive microorganism used for the production of L-amino acid. L-amino acid, particularly L-lysine, has been widely used for the production of animal feeds, medicines for humans, and cosmetics. This amino acid is generated by the fermentation using Corynebacterium.

The conventional production method of L-lysine has used Corynebacterium having enhanced L-lysine biosynthesis related gene. For example, U.S. Pat. No. 6,746,855 describes a production method of L-lysine by culturing Corynebacterium sp. which enhanced the lysine releasing carrier gene lysE and introduced with an additional gene selected from the group consisting of dapA encoding dihydrodipicolinate synthase, lysC encoding aspartate kinase, pyc encoding pyruvate carboxylase and dapB encoding dihydropicolinate reductase. And, U.S. Pat. No. 6,221,636 describes Corynebacteria transformed with recombinant DNA containing the DNA sequence encoding diaminopimelate dicarboxylase and the DNA sequence encoding aspartokinase which is substantially insensitive to feedback inhibition by L-lysine and L-threonine.

To enhance the L-lysine biosynthesis related gene without an antibiotic-resistant sequence, either the number of gene copies is increased or the enzyme activity is increased by mutation. There are two methods reported so far to increase the number of gene copies.

One of the two methods to increase the number of copies is tandem repeat which inserts an additional gene into the right next to the intrinsic gene. The other method is to insert an additional gene into one or more chromosome regions of Corynebacterium sp. (U.S. Pat. No. 7,160,711). However, these methods are limited in gene insertion sites, indicating that it is very difficult to insert multiple genes. To overcome this problem, it has been attempted to insert target genes in the region of multiple copies of rDNA on the genome. It was reported that this method was more successful than the previous ones. Nevertheless, this method has still a limitation because the destruction of two or more rDNA copies can affect the growth of the microorganism.

Transposon is also called Insertional Sequence Element, which is the sequence that can move on a chromosome or a plasmid. Transposon contains a DNA sequence including a transposase-encoding gene flanked by two inverted repeat (IR) sequences which are located in opposite directions (FIG. 10). Transposase can act to recognize the terminal IR sequences of transposon and copy or move the transposon to a new chromosomal location. Up to date, hundreds of transposons have been found in a variety of bacteria (TRANSPOSON-BASED STRATEGIES FOR MICROBIAL FUNCTIONAL GENOMICS AND PROTEOMICS (2003) Annual Review of Genetics 37: 3-29 Finbarr Hayes).

SUMMARY OF THE INVENTION

The present inventors have made extensive efforts develop a strain, which can produce lysine at high concentration, using a transformation vector which can insert two or more copies of a target gene into any location of the strain without inhibiting the growth of the microorganism. As a result, the present inventors have found that a transformation vector comprising a transposon gene is useful for the introduction of a foreign gene, thereby completing the present invention.

Therefore, it is an object of the present invention to provide a method of inactivating a transposase in the chromosome of a Corynebacterium sp. microorganism and expressing a target gene in the Corynebacterium sp. microorganism, the method comprising the steps of: 1) introducing the target gene into a gene encoding the transposase in the chromosome of the Corynebacterium sp. microorganism to transform the Corynebacterium sp. microorganism; and 2) culturing the transformed microorganism.

It is another object of the present invention to provide a Corynebacterium sp. microorganism having an increased ability to produce lysine, the microorganism being provided by the above method.

It is further an object of the present invention to provide a production method of lysine from the culture solution of the Corynebacterium sp. microorganism.

To achieve the above objects, the present invention provides a method of inactivating a transposase in the chromosome of a Corynebacterium sp. microorganism and expressing a target gene in the Corynebacterium sp. microorganism, the method comprising the steps of: 1) introducing the target gene into a gene encoding the transposase in the chromosome of the Corynebacterium sp. microorganism to transform the Corynebacterium sp. microorganism; and 2) culturing the transformed microorganism.

The present invention also provides a Corynebacterium sp. microorganism having an increased ability to produce lysine, the microorganism being provided by the above method.

The present invention also provides a method of producing lysine, comprising culturing the above Corynebacterium sp. microorganism and recovering lysine from the culture broth.

ADVANTAGEOUS EFFECT

The present invention provides a Corynebacterium sp. microorganism capable of producing amino acids, particularly lysine, at high concentration that has improved endogenous activity by inserting target genes, particularly genes related to amino acid productions, aspartate kinase gene (lysC), aspartate semialdehyde dihydrogenase gene (asd), dihydrodipicolinate synthase gene (dapA) and dihydropicolinate reductase gene (dapB) serially in the region of a transposon gene existing as multiple copies on the genome of the Corynebacterium sp. microorganism and at the same time has been endowed a novel activity by the additional insertion of fructokinase gene (srk) not existing in *Corynebacteria* in the region of the transposon gene.

BRIEF DESCRIPTION OF THE DRAWINGS

The above and other objects, features and advantages of the present invention will become apparent from the following description of preferred embodiments given in conjunction with the accompanying drawings, in which.

DETAILED DESCRIPTION OF THE INVENTION

Figure 1:
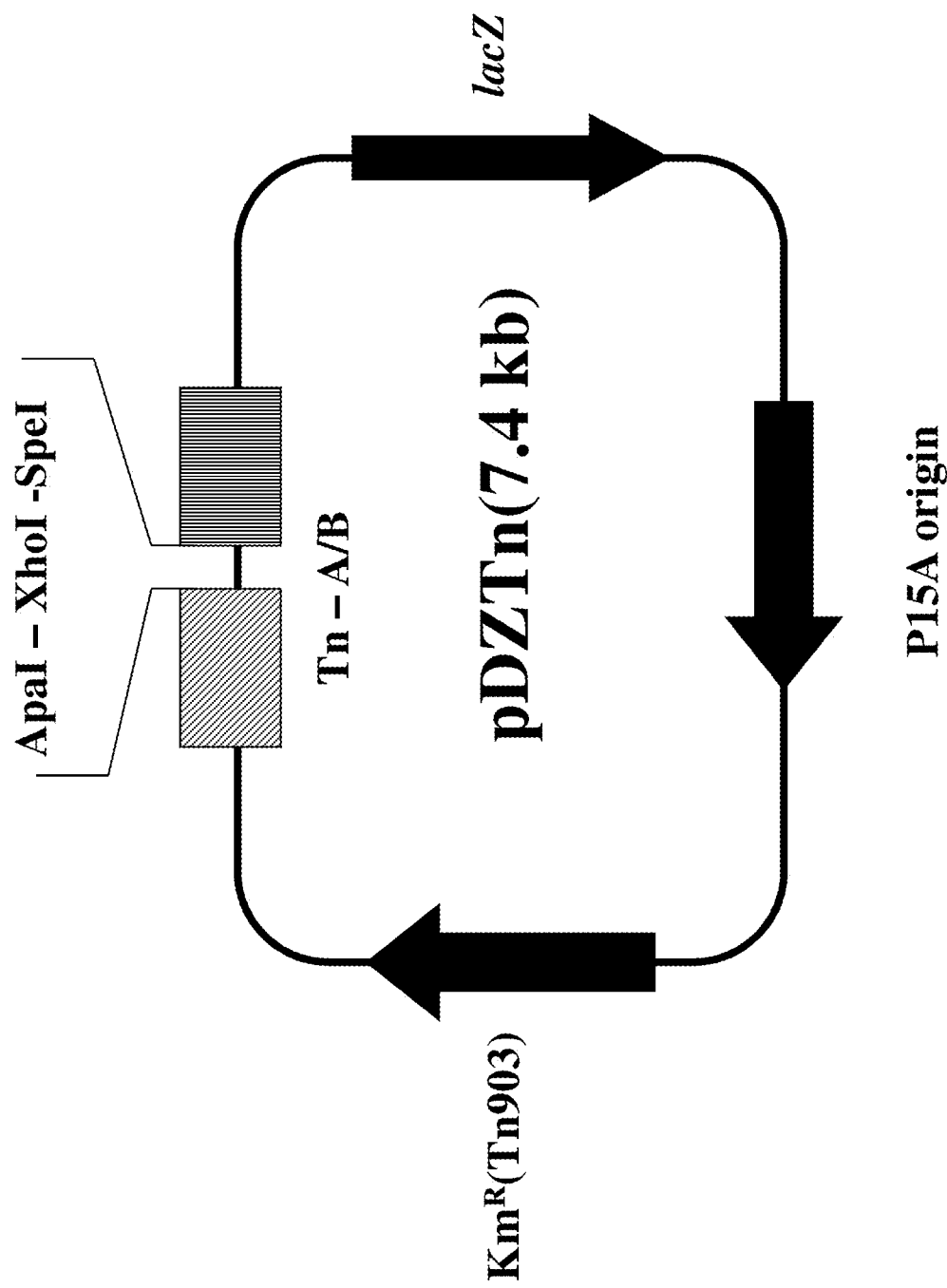
FIG. 1 shows the vector pDZTn for insertion into the *Corynebacterium* chromosome, in which the vector contains a plurality of restriction sites and has a partial fragment of gene encoding transposase.

The present invention provides a transformation vector containing a multi-cloning site in between the 5' terminal and 3' terminal fragment of a gene encoding transposase.

The gene encoding transposase can be originated from *Corynebacterium* sp. *Corynebacterium* sp. microorganism has many different types of transposons. For example, *Corynebacterium glutamicum* ATCC13032 includes 24 transposons, which are classified into 9 groups (The complete *Corynebacterium glutamicum* ATCC 13032 genome sequence and its impact on the production of -aspartate-derived amino acids and vitamins (2003) *Journal of Biotechnology* 104, 5-25 Jorn Kalinowski et al). Among them, ISCg1 and ISGg2 include 4 and 5 copies respectively and each copy shows at least 99% homology.

*Corynebacterium* sp. microorganisms may have a transposon of ISCg1 and ISCg2 type on the chromosome. The transposon contains a DNA sequence including transposase-encoding gene flanked by two inverted repeat (IR) sequences which are located in opposite directions. Herein, a sequence encoding the transposases of the ISCg1 type may have a nucleic acid sequence set forth in SEQ ID NO: 22, and a sequence encoding the transposase of the ISCg2 type may have a nucleic acid sequence set forth in SEQ ID NO: 29. Preferably, the transposase-encoding gene of the present invention belongs to the ISCg1 type (SEQ ID. NO: 22) among transposons originated from *Corynebacterium glutamicum* ATCC13032 (GenBank accession NO: NC_003450, NCgl1021), and particularly, may have a nucleic acid sequence of SEQ ID. NO: 1, 2, 23 or 24. When the transposase-encoding gene of the present invention belongs to the ISCg2 type, it may preferably have a nucleotide sequence of SEQ ID NO: 34 or 35.

The multi-cloning site is a nucleotide sequence which is artificially inserted so as to be able to be recognized by a plurality of restriction enzymes, and it functions to facilitate the insertion of a target gene. In the present invention, the multi-cloning site only functions to facilitate the insertion of a target gene into the open reading frame of the transposase gene contained in the transformation vector. The types of restriction enzymes that can recognize the nucleotide and sugar sequences of the multi-cloning site are not limited to those described in the Examples of the present invention, and any restriction enzymes may be used in the present invention. Also, when just the multi-cloning site is inserted, the transposase gene contained in the transformation vector according to the present invention can be provided in a state in which it lost its original function due to the discontinuous separation of the transposase protein-encoding sequence and the change in the corresponding codon by frame-shift.

In the present invention, the phrase "inactivation of a gene" means that the expression of the gene of interest is reduced or silenced by one or more mutations selected from the group consisting of all or part of the gene, substitution of part of the nucleotide sequence, and insertion of one or more base pairs into the nucleotide sequence, whereby the activity of a protein encoded by the gene is reduced or disrupted. In the present invention, the phrase "inactivation of transposon" ultimately means the inactivation of transposase gene and includes a process in which the expression of transposase gene is silenced by the insertion of a multi-cloning site or a target gene into the transposase gene, and thus the transposase gene loses the function to replicate and move in a chromosome. Thus, the cell physiological activity and target product productivity of a microorganism lacking transposase function are stably maintained compared to those of a microorganism retaining transposase function, suggesting that this microorganism is an industrially useful microbial strain.

In the present invention, a target gene that can be inserted into the multi-cloning site may be not only an endogenous gene, but also an exogenous gene. Specific examples thereof aspB (gene encoding aspartate aminotransferase), lysC (gene encoding aspartate kinase), asd (gene encoding aspartate semialdehyde dehydrogenase), dapA (gene encoding dihydrodipicolinate synthase), dapB (gene encoding dihydropicolinate reductase) and lysA (gene encoding diaminodipymalate dicarboxylase), which are endogenous genes of *Corynebacterium* sp. microorganisms involved in the production of L-amino acid, as well as exogenous genes such as exogenous srk (gene encoding fructokinase).

It is preferable to insert one or more genes selected from the group consisting of aspB, lysC, asd, dapA, dapB and lysA into the multi-cloning site. It is also possible to insert the endogenous genes selected above and an exogenous gene together into the multicloning site. It is more preferred to serially insert lysC/asd and dapA/dapB into the multicloning site or possibly the exogenous srk gene that cannot be found in *Corynebacterium* sp. microorganisms is inserted.

In a preferred embodiment of the present invention, the lysC, asd, dapA, and dapB genes have the nucleotide sequences respectively represented by SEQ ID. NOs: 17, 18, 19, and 20 originated from *Corynebacterium glutamicum* KCCM 10770Pb (GenBank accession number: NC_003450, NCgl0247~0248 and NCgl1896~1898). The foreign gene srk can have the nucleotide sequence represented by SEQ ID.

NO: 21 originated from *Clostridium acetylbutyricum* ATCC 824 (GenBank accession number: NP_347064), but is not limited thereto.

The genes inserted into the transformation vector of the present invention can be incorporated intact into the chromosome of *Corynebacterium* sp. microorganisms by a secondary homologous recombination method known in the art. Herein, the transposase-encoding gene fragments in the transformation vector are only used as homologous nucleotide sequence structures for inducing homologous recombination with the chromosome. When the transformation vector is introduced into *Corynebacterium*, homologous recombination between the common nucleotide sequences of transposase-encoding genes in the chromosome and transposase-encoding gene fragments (5' and 3' fragments) in the transformation vector occurs. By such a series of recombination procedures, the target gene located between the transposase-encoding gene fragments in the vector is inserted into the transposase-encoding gene in the chromosome of microorganisms.

The vector for transformation comprising the transposon gene according to the present invention is not only able to amplify at least two copies of the endogenous gene but also suitable for the insertion of gene by crossover with high efficiency owing to the multiple transposons. This vector can also be effective in producing a strain that can amplify different genes in a series with the same vector. The transposon is the gene that does not affect the growth of a microorganism and is rather helpful to reduce gene instability. Moreover, it facilitates foreign gene insertion even without a specific target site and it can also be prepared in a series.

The present invention also provides a *Corynebacterium* sp. microorganism transformed with the above transformation vector and having improved lysine productivity.

As used herein, the term "transformation" means any action that introduces a gene into the host *Corynebacterium* sp. strain such that the gene can be expressed in the host cell. Herein, the promoter and the gene are polynucleotides, including DNA and RNA. The gene may be introduced in any form, as long as it can be introduced and expressed in a host cell. For example, the gene can be introduced into the host cell in the form of an expression cassette which is a polynucleotide structure containing all elements required for the expression of the gene. The expression cassette generally contains a promoter operably linked to the gene, a transcription termination signal, and RBS and translation termination signals. The gene may be introduced alone or in the form of a polynucleotide structure into the host cell.

Methods of transformation with the vector of the present invention include any method for introducing a nucleic acid into a cell and can be carried out using known suitable standard technology selected depending on a host cell. Examples of the method include electroporation, calcium phosphate ($CaPO_4$) precipitation, calcium chloride ($CaCl_2$) precipitation, microinjection, a polyethyleneglycol (PEG) method, a DEAE-dextran technique, a cationic liposome technique and a lithium acetate-DMSO technique.

In this invention, the microorganism having lysine productivity that can be transformed by the vector for transformation of the present invention can be any of those *Corynebacterium* sp. microorganisms. For example, the *Corynebacterium* sp. microorganism that is available for this invention is *Corynebacterium glutamicum* ATCC 13032 or *Corynebacterium thermoaminogenes* PERM BP-1539. Besides, the L-amino acid producing mutants or strains generated therefrom, for example *Corynebacterium glutamicum* KFCC10881, *Corynebacterium glutamicum* KFCC 11001 and *Corynebacterium glutamicum* KCCM 10770 are also available. Most preferably, the microorganism is *Corynebacterium glutamicum* KCCM 10770P.

Figure 2:
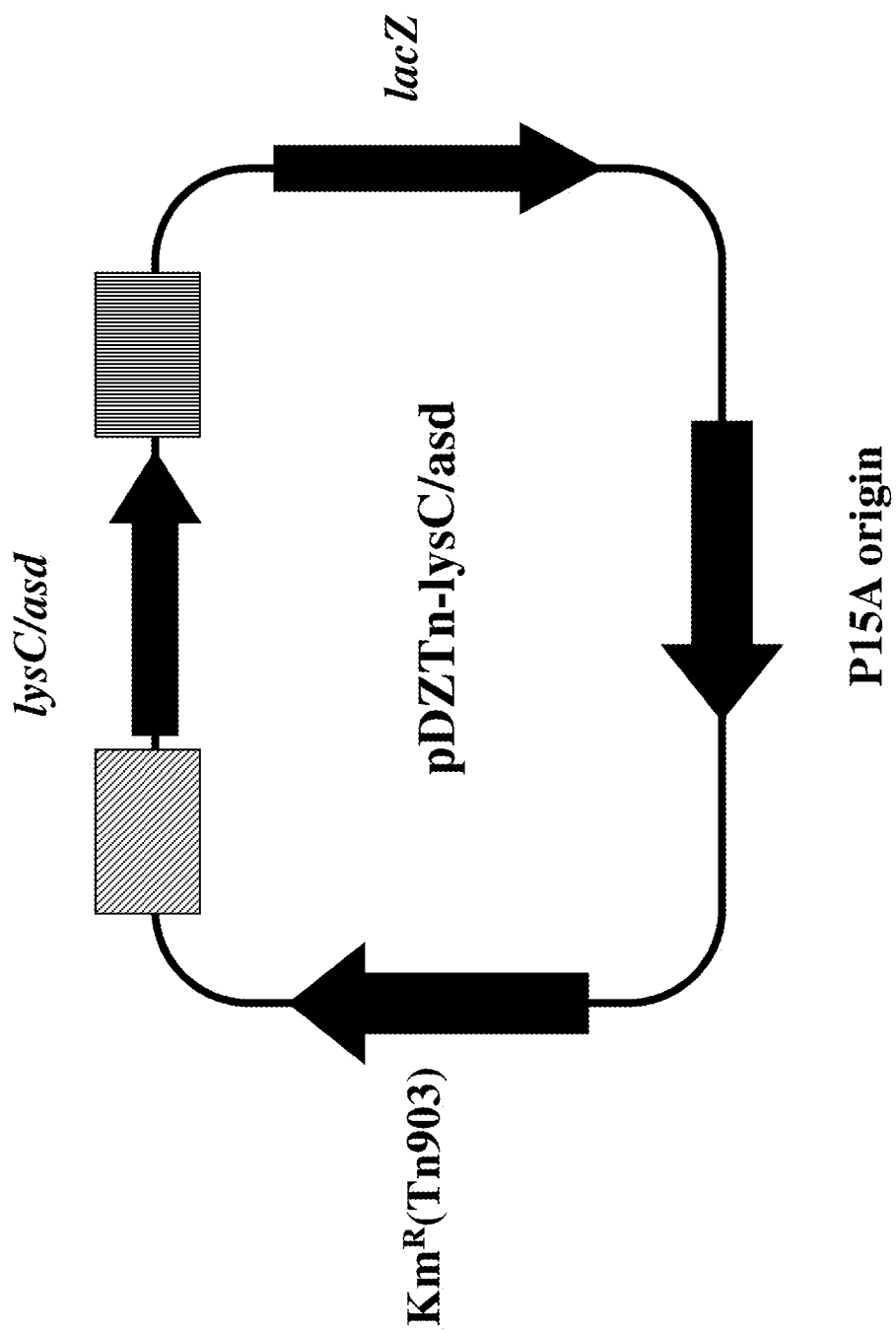
FIG. 2 shows the vector pDZTn-lysC/asd for insertion into the *Corynebacterium* chromosome.
Figure 3:
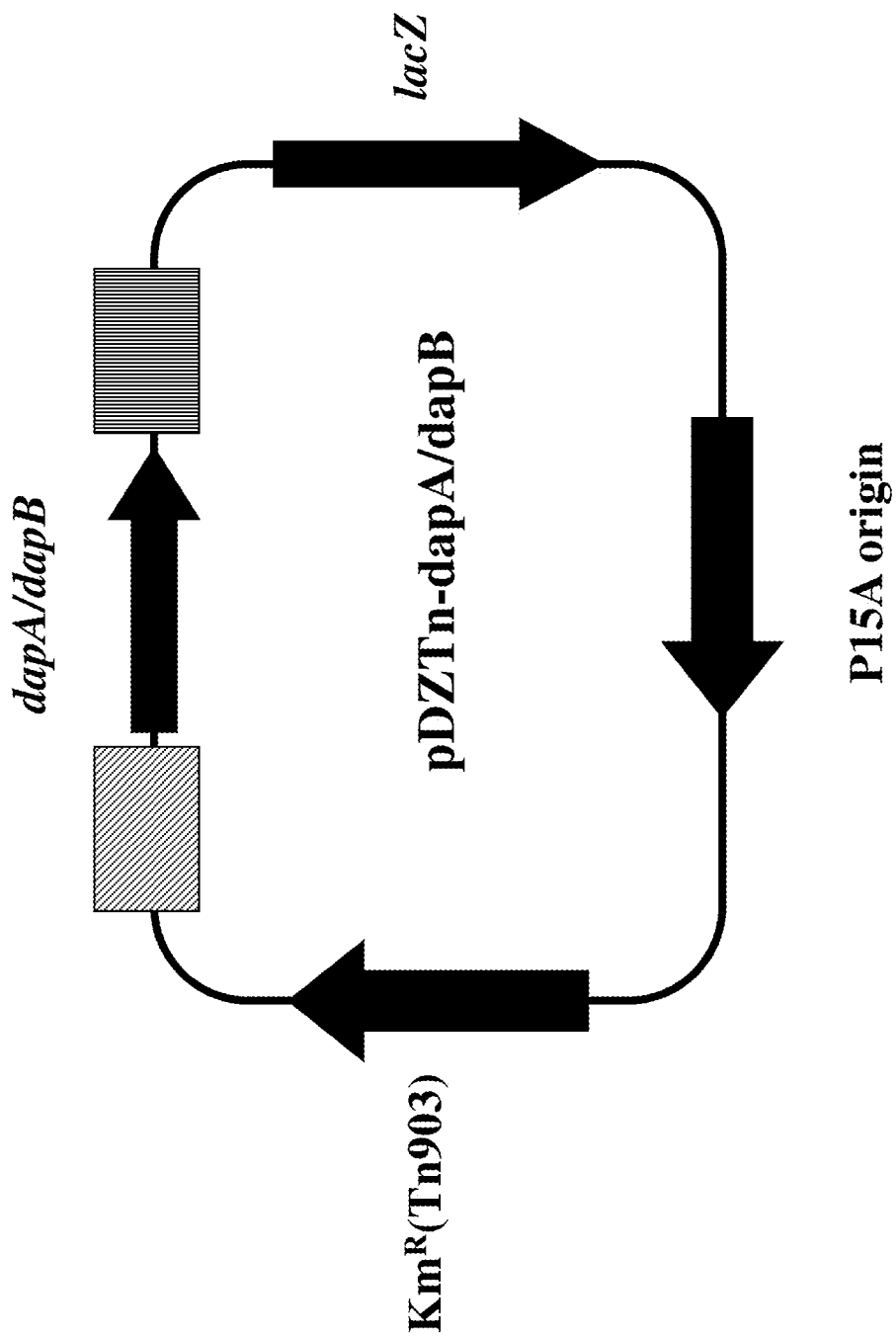
FIG. 3 shows the vector pDZTn-dapA/dapB for insertion into the *Corynebacterium* chromosome.
Figure 4:
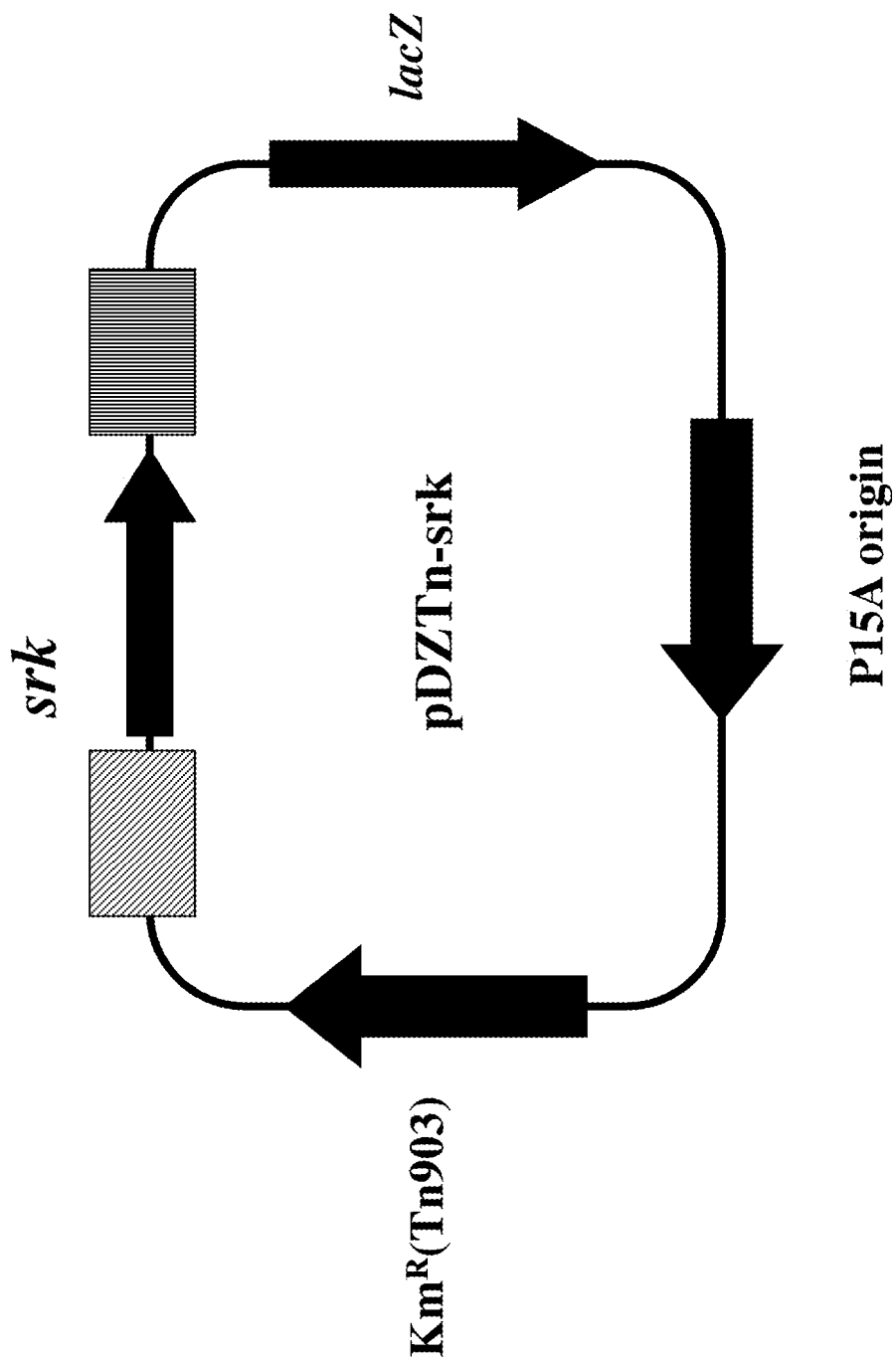
FIG. 4 is a diagram illustrating pDZTn-srk vector.

In a preferred embodiment of the present invention, the *Corynebacterium* sp. microorganism of the invention can be transformed by the vector for transformation pDZTn-lscC/asd, pDZTndapA/dapB or pDZTn-crk having the cleavage map of FIG. 2, 3, or 4. The vector for transformation can be inserted in the *Corynebacterium* sp. microorganism orderly or simultaneously. The insertion of the vector into chromosome can be performed by the method well-known to those in the art such as homologous recombination.

The present invention further provides a production method of lysine from the culture solution of the *Corynebacterium* sp. microorganism.

The culture of L-lysine using the *Corynebacterium* sp. microorganism can be performed by the conventional method well-known to those in the art. For example, the culture herein can be performed by fed batch or repeated fed batch process.

The medium used for the culture herein has to fit the condition required for the specific strain by a required process. The culture medium for the *Corynebacterium* sp. strain is well informed (for example, Manual of Methods for General Bacteriology. American Society for Bacteriology. Washington D.C., USA, 1981).

The usable glycogen is exemplified by carbohydrate such as glucose, sucrose, lactose, fructose, maltose, starch, cellulose; oil and fat such as soybean oil, sunflower oil, castor oil and coconut oil; fatty acid such as palmitic acid, stearic acid, and linoleic acid; alcohol such as glycerol and ethanol; and organic acid such as acetic acid. One of these compounds or a mixture thereof can be used.

The usable nitrogen source is exemplified by such organic nitrogen source as peptone, yeast extract, gravy, malt extract, corn steep liquor and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source.

The medium herein can additionally include potassium dihydrogen phosphate, dipotassium hydrogen phosphate and corresponding sodium-containing salts as a phosphate source. The medium can also include a metal salt such as magnesium sulfate or iron sulfate. In addition, amino acids, vitamins and proper precursors can be added as well. The medium or the precursor can be added to the culture by batch-type or continuously. pH of the culture can be adjusted during the cultivation by adding such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas (eg, air) can be injected into the culture. The temperature of the culture is preferably 20-45° C., more preferably 25-40° C. The cultivation can be continued until the production of L-amino acid reaches a wanted level, and the preferable culture time is 10-160 hours. L-lysine is released in the culture medium or can be included in cells.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Genetic Information of Transposase

It is known that wild-type *Corynebacterium glutamicum* has three kinds of transposase genes. To obtain a transposase genes, the nucleotide sequence information of transposase genes (NCBI accession No: NC_003450 and NCgl1021, SEQ ID NO: 22) was obtained from the total nucleotide sequence derived from *Corynebacterium glutamicum* ATCC 13032 on the basis of NM GenBank, and the genes were named "group 1 transposase". The obtained transposase gene (NCgl1021) was searched against KEGG SSDW paralog(// www.kegg.jp/ssdb-bin/ssdb_paralog?org_gene=cgl: NCgl1021), and as a result, it was found that the gene has a very high identity of 99% or more with the two other genes (NCgl2284, and NCgl2392).

TABLE 1

SSDW Paralog Search Result: KEGG ID NCgl1021 (436 aa)

|  | length (aa) | SW-score | identity | overlap |
|---|---|---|---|---|
| NCgl2392 | 436 | 2974 | 1.000 | 436 |
| NCgl2284 | 436 | 2968 | 0.998 | 436 |

Another transposase gene (NCgl0179, SEQ ID NO: 29) was searched for gene identity in the same manner as above. As a result, two genes (NCgl2131, and NCgl2748, Table 2) having high identity were obtained and named "group 2 transposase".

TABLE 2

SSDW Paralog Search Results: KEGG ID NCgl0179 (536 aa)

|  | length (aa) | SW-score | identity | overlap |
|---|---|---|---|---|
| NCgl2131 | 536 | 3558 | 1.000 | 536 |
| NCgl2748 | 401 | 2663 | 1.000 | 401 |

Example 2

Construction of the Vector (pDZTn) Introduced with Transposase Gene and the Method for Inserting Gene Using the Vector In this example, the pDZ vector (Korean Patent No. KR0924065) for insertion of the chromosome of *Corynebacterium* sp. microorganisms was used as a basic vector to construct the vector pDZTn introduced with the transposase gene of *Corynebacterium* sp. The construction process is as follows.

To obtain transposase gene, the nucleotide sequence information about the transposase gene (NCBI accession NO. NC_003450, NCgl1021) of the total nucleotide sequence originated from *Corynebacterium glutamicum* ATCC13032 was obtained from NIH GenBank, and based on this information, two pairs of primers (Table 1, SEQ ID. NOs: 3 to 6) were synthesized.

PCR was performed using the chromosomal DNA of *Corynebacterium glutamicum* ATCC13032 as a template and the oligonucleotides represented by SEQ ID. NOs: 3 to 6 as primers. PfuUltra™ high-fidelity DNA polymerase (Stratagene) was used as the polymerase. PCR conditions were as follows: 30 cycles each consisting of denaturation at 96° C. for 30 seconds, annealing at 58° C. for 30 seconds, and polymerization at 72° C. for 1 minute.

TABLE 3

| Primer | Sequence | SEQ ID. NO: |
|---|---|---|
| Tn-A-F | atcctctagagtcgaccatcgctgacaccatctgcc | 3 |
| Tn-A-R | gggcccactagtctcgagttcaccgcgggagccaagcc | 4 |
| Tn-B-F | ctcgagactagtgggcctggattccaaggctacgcc | 5 |
| Tn-B-R | atgcctgcaggtcgaccctgaatggataaggcaccg | 6 |

As a result, two transposase gene fragments (Tn-A and Tn-B) having a size of about 500 bp and containing a promoter region were obtained. Tn-A (SEQ ID. NO: 1) was obtained by amplification using the primer sequences represented by SEQ ID. NOs: 3 and 4, while Tn-B (SEQ ID. NO: 2) was obtained by amplification using the primer sequences represented by SEQ ID. NO: 5 and 6. The two gene fragments are transposase gene fragments. The amplified products were cloned into a pDZ vector pretreated with Sal I restriction enzyme using BD in-Fusion kit (BD), thereby constructing a pDZTn vector. There are numbers of restriction enzyme recognition sites, artificially inserted during the primer construction, between the two amplified products.

FIG. 1 shows the vector pDZTn for insertion into the *Corynebacterium* chromosome, in which the vector contains a plurality of restriction enzyme recognition sites and has partial fragments of gene encoding transposase.

*Corynebacterium glutamicum* KCCM10770P, the patented lysine-production strain, was transformed with the pDZTn vector constructed by inserting the target genes (Tn-A and Tn-B) (using the transformation method of Appl. Microbiol. Biotechnol. (1999) 52:541-545). Then, the strain having the target gene inserted by gene homology on the chromosome was selected from the selection medium containing 25 mg/L of kanamycin. The successful insertion of the vector in the chromosome was confirmed by observing if the colony was blue on the solid medium containing X-gal (5-bromo-4-chloro-3-indolyl-β-D-galactoside). The primary chromosome inserted strain was shaking-cultured in a nutrient medium (30° C., 8 hours), which was then diluted from $10^{-4}$ to $10^{-10}$, followed by distribution on the solid medium containing X-gal. While most colonies were blue, there were some colonies that were white. Those low rate white colonies were selected, which proceeded to the selection of the strain whose vector sequence inserted on the chromosome was eliminated by the secondary crossover.

Example 3

Construction of Another Vector (pDZTn300) Containing Partial Fragments of Group 1 Transposase Gene In this Example, using the pDZ vector for insertion of the chromosome of *Corynebacterium* sp. microorganisms as a basic vector, the vector pDZTn300 containing the transposase gene of *Corynebacterium* sp microorganisms was constructed in the following manner. The vector constructed in this Example differs in the sizes of inserted transposase gene fragment from the vector constructed in Example 2.

On the basis of the nucleotide sequences of transposase gene obtained in the above Example, two primer pairs were synthesized (Table 4, SEQ ID NOS: 25 to 28). PCR was performed using the chromosomal DNA of *Corynebacterium glutamicum* ATCC13032 as a template and the oligonucleotides of SEQ ID NOS: 25 to 28 as primers. The PCR was performed using PfuUltra™ high-fidelity DNA polymerase (Stratagene) for 30 cycles, each consisting of denaturation at 96° C. for 30 sec, annealing at 58° C. for 30 sec, and polymerization at 72° C. for 30 sec.

TABLE 4

| Primer | Nucleotide sequence | SEQ ID NO |
|---|---|---|
| Tn300-A-F | a tcc tct aga gtc gac atagggctaagcatggtgat | 25 |
| Tn300-A-R | gggcccactagtctcgag cgctggtatttctcccgctgg | 26 |
| Tn300-B-F | ctcgagactagtgggccc gattattgattgttatcagat | 27 |
| Tn300-B-R | a tgc ctg cag gtc gac tgatcttatggaccaactgccc | 28 |

As a result, two DNA fragments of transposase gene (Tn300-A and Tn300-B) having a size of about 300 bp were obtained. Tn300-A (SEQ ID NO: 23) was obtained by amplification using the primer sequences of SEQ ID NOS: 25 and 26, and Tn300-B (SEQ ID NO: 24) was obtained by amplification using the primer sequences of SEQ ID NOS: 27 and 28. The two DNA fragments are a fragment in the transposase gene. The amplification products were cloned into a pDZ treated with a SalI restriction enzyme using the BD In-Fusion kit (BD), thereby obtaining a pDZTn300 vector. The region between the two amplification products contains a number of the restriction sites inserted during the construction of the primers.

FIG. 2 shows the vector pDZTn300 for insertion into the *Corynebacterium* chromosome, in which the vector contains a plurality of restriction enzyme recognition sites and has a part of gene encoding transposase.

Example 4

Construction of Vector (pDZTn2) Containing Partial Fragments of Group 2 Transposase Gene In this Example, using the pDZ vector for insertion of the chromosome of *Corynebacterium* sp. microorganisms as a basic vector, the vector pDZTn2 containing the group 2 transposase gene of *Corynebacterium* sp microorganisms was constructed in the following manner.

Based on the nucleotide sequence of group 2 transposase gene (NCgl0179, SEQ ID NO: 29), two primer pairs (Table 5, SEQ ID NOS: 30 to 33) were synthesized.

PCR was performed using the chromosomal DNA of *Corynebacterium glutamicum* ATCC13032 as a template and the oligonucleotides of SEQ ID NOS: 30 to 33 as primers. The PCR was performed using PfuUltra™ high-fidelity DNA polymerase (Stratagene) for 30 cycles, each consisting of denaturation at 96° C. for 30 sec, annealing at 58° C. for 30 sec, and polymerization at 72° C. for 30 sec.

TABLE 5

| Primer | Nucleotide sequence | SEQ ID NO |
|---|---|---|
| Tn2-A-F | a tcc tct aga gtc gac cacgcacactccatcaagtg | 30 |
| Tn2A-R- | tCTCGAGACTAGTGGGCCgcatagagctatcgttagcatg | 31 |
| Tn2-B-F | cGGCCCACTAGTCTCGAGagaggtaagccgtgggtggagggtgcg | 32 |
| Tn2-B-R | a tgc ctg cag gtc gac gtaattcagcagatcctgtgc | 33 |

As a result, two DNA fragments of transposase gene (Tn2-A and Tn2-B) having a size of about 300 bp were obtained. Tn2-A (SEQ ID NO: 34) was obtained by amplification using the primer sequences of SEQ ID NOS: 30 and 31, and Tn2-B (SEQ ID NO: 35) was obtained by amplification using the primer sequences of SEQ ID NOS: 32 and 33. The two DNA fragments are a fragment in the transposase gene. The amplification products were cloned into a pDZ treated with a SalI restriction enzyme using the BD In-Fusion kit (BD), thereby obtaining a pDZTn2 vector. The region between the two amplification products contains a number of the restriction enzyme recognition sites inserted during the construction of the primers.

FIG. 3 shows the vector pDZTn2 for insertion into the *Corynebacterium* chromosome, in which the vector contains a plurality of restriction enzyme recognition sites and has partial fragments of transposase gene.

Example 5

Cloning of dapA/dapB Originated from the Lysine Production Strain *Corynebacterium glutamicum* KCCM10770P, Construction of the Recombinant Vector (pDZTn-dapA/dapB), and Development of the dapA/dapB Inserted Strain To obtain dapA/dapB gene originated from *Corynebacterium glutamicum* KCCM 10770P by the same manner as described in example 2, nucleotide sequence information of dapA/dapB (NCBI accession NO. NC_003450, Ncgl1896~1898) was obtained from NIH GenBank. As a result, it was confirmed that dapA composed operon along with dapB, between which there was ORF (Ncgl1987) whose functions had not been disclosed, yet. Therefore, to amplify the total gene dapB-ORF (Ncgl1897)-dapA containing dapB promoter region, two pairs of primers were synthesized (Table 6, SEQ ID NOs: 11-12).

PCR was performed using the chromosomal DNA of *Corynebacterium glutamicum* KCCM10770P as a template and the oligonucleotides represented by SEQ ID. NO: 11 to 12 as primers. PfuUltra™ high-fidelity DNA polymerase (Stratagene) was used as a polymerase. PCR conditions were as follows: 30 cycles each consisting of denaturation at 96° C. for 30 seconds, annealing at 52° C. for 30 seconds, and polymerization at 72° C. for 3 minutes.

TABLE 6

| Primer | Sequence | SEQ ID. NO: |
|---|---|---|
| dapA-F (SpeI) | tgtcgggcccactagttcattggcgtttccggatcc | 11 |
| dapA-R (XhoI) | gaatgagttcctcgagacaagcgccaaggaactacc | 12 |

As a result, a 2,805-bp lysC/asd gene containing a promoter region was produced. The amplification product was cloned into a pDZTn vector and a pDZTn2 vector, which had been treated with the restriction enzymes SpeI and XhoI, using the BD In-Fusion kit, thereby obtaining a pDZTn-lysC/asd recombinant vector and a pDZTn2-lysC/asd recombinant vector.

FIG. 4 shows the vector pDZTn-lysC/asd for insertion into the *Corynebacterium* chromosome.

Figure 5:
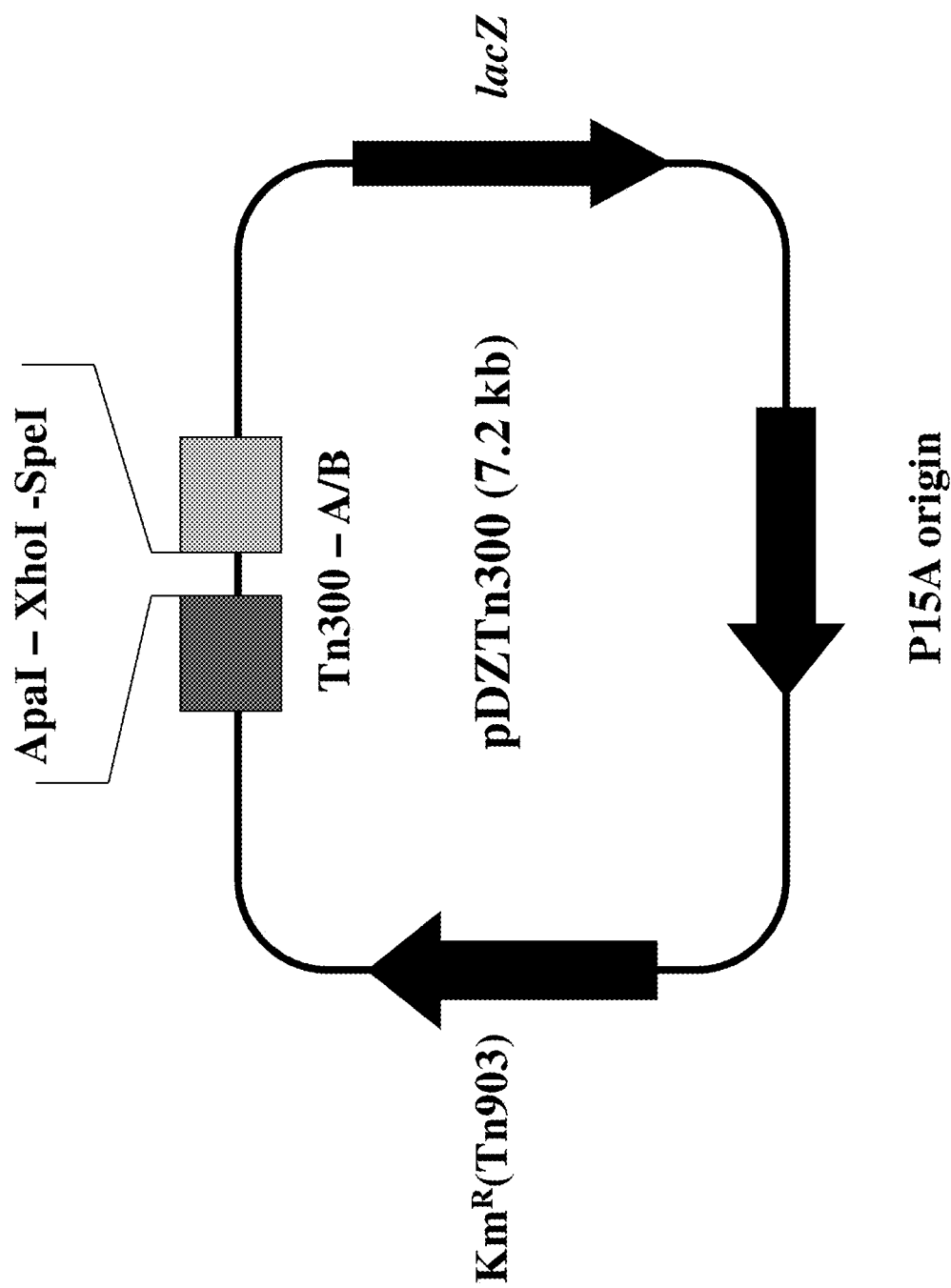
FIG. 5 shows the vector pDZTn300 for insertion into the *Corynebacterium* chromosome, in which the vector contains a plurality of restriction sites and has a partial fragment of gene encoding transposase.

FIG. 5 shows the vector pDZTn2-lysC/asd for insertion into the *Corynebacterium* chromosome.

Each of the constructed pDZTn-lysC/asd vector and pDZTn2-lysC/asd vector was transformed into wild type *Corynebacterium glutamicum* ATCC13032, followed by secondary crossover, thereby obtaining the transformed strains *Corynebacterium glutamicum* ATCC13032-CJ1 and ATCC13032-CJ2 containing the lysC/asd gene between the transposase genes in the chromosome. The obtained strains were confirmed by PCR using the primers of SEQ ID NOS: 9, 10 and 36 (Table 7) capable of amplifying a region of the transposon and lysC/asd genes. pDZTn-lysC/asd was confirmed using the primer of SEQ ID NOS: 9 and 10, and pDZTn2-lysC/asd was confirmed using the primers of SEQ ID NOS: 36 and 10.

There was no difference in a strain construction process between the two vectors containing the transposase genes of different groups.

TABLE 7

| Primer | Nucleotide sequence | SEQ ID NO |
|---|---|---|
| Tn-A-F | gctaccgctgcaccaacccc | 9 |
| Tn2-A-F | cacgcacactccatcaagtg | 36 |
| asd-1 | ttc acg ccg aat tcg aca agg caa tca ccg | 10 |

*Corynebacterium glutamicum* KCCM10770P, the patented lysine production strain was transformed with the constructed vector pDZTn-lysC/asd. After the secondary crossover, a copy of lysC/asd gene was additionally inserted in between transposases on the chromosome. As a result, the lysine production strain *Corynebacterium glutamicum* KCCM10770P-CJ1 having three copies of the gene was prepared. To confirm the strain, PCR was performed using primer 9 and primer 10 (Table 7) facilitating the amplification of the joining region between the transposase and lysC/asd gene.

Example 5

Cloning of dapA/dapB Originated from the Lysine Production Strain *Corynebacterium glutamicum* KCCM10770P, Construction of the Recombinant Vector (pDZTn-dapA/dapB), and Development of the dapA/dapB Inserted Strain To obtain dapA/dapB gene originated from *Corynebacterium glutamicum* KCCM 10770P by the same manner as described in example 2, nucleotide sequence information of dapA/dapB (NCBI accession NO. NC_003450, Ncgl1896~1898) was obtained from NIH GenBank. As a result, it was confirmed that dapA composed operon along with dapB, between which there was ORF (Ncgl1987) whose functions had not been disclosed, yet. Therefore, to amplify the total gene dapB-ORF (Ncgl1897)-dapA containing dapB promoter region, two pairs of primers were synthesized (Table 8, SEQ ID. NO: 11-12).

PCR was performed using the chromosome DNA of *Corynebacterium glutamicum* KCCM10770P as a template and using the oligonucleotides represented by SEQ ID. NO: 11-12 as primers. PfuUltra™ high-confident DNA polymerase (Stratagene) was used as a polymerase. PCR conditions were as follows; denaturation at 96° C. for 30 seconds, annealing at 52° C. for 30 seconds, polymerization at 72° C. for 3 minutes, and 30 cycles from denaturation to polymerization.

TABLE 8

| Primer Sequence | SEQ ID. NO: |
|---|---|
| dapA-F tgtcgggcccactagttcattggcgtttccggatcc (SpeI) | 11 |
| dapA-R gaatgagttcctcgagacaagcgccaaggaactacc (XhoI) | 12 |

As a result, dapA/dapB gene containing 3,210 bp long promoter region was separated. The amplified product was cloned into pDZTn vector pretreated with Spe I and Xho I using BD in-Fusion kit, resulting in the construction of the recombination vector pDZTn-dapA/dapB. FIG. 3 shows the *Corynebacterium* chromosome insertion vector pDZTn-dapA/dapB.

The lysine production strain *Corynebacterium glutamicum* KCCM10770P-CJ1 prepared in example 2 was transformed with the constructed vector pDZTn-dapA/dapB. After the secondary crossover, a copy of dapA/dapB gene was additionally inserted in between transposons on the chromosome. As a result, the lysine production strain *Corynebacterium glutamicum* KCCM10770P-CJ2 having three copies of the gene was prepared. To confirm the strain, PCR was performed using primer 9 and primer 13 (Table 9) facilitating the amplification of the joining region between the transposon and dapA/dapB gene.

TABLE 9

| Primer | Sequence | SEQ ID. NO: |
|---|---|---|
| Tn-A-F | gctaccgctgcaccaacccc | 9 |
| dapA-1 | acaagcgccaaggaactacc | 13 |

Example 6

Cloning of srk Originated from *Clostridium acetobutylicum*, Construction of the Recombinant Vector (pDZTn-srk) and Development of the srk Inserted Strain The nucleotide sequence of fructokinase gene originated from *Clostridium acetobutylicum* ATCC 824 has been well-known. The present inventors obtained the gene information of fructokinase originated from *Clostridium acetobutylicum* ATCC 824 from NIH GenBank (Accession NO. NP_347064). A pair of primers (Table 10, SEQ ID NOs: 14 and 15) was synthesized according to the obtained nucleotide sequence. PCR was performed using the chromosome DNA of *Clostridium acetobutylicum* ATCC 824 as a template to amplify the gene. PCR conditions were as follows; denaturation at 94° C. for 20 seconds, annealing at 52° C. for 20 seconds, polymerization at 72° C. for 1 minute and 10 seconds, and 30 cycles from denaturation to polymerization.

TABLE 10

| Primer | Sequence | SEQ ID. NO: |
|---|---|---|
| Srk-F(SpeI) | tgtcgggcccactagtcatatgaataatgttttatgtatgggagaa | 14 |
| srk-R(XhoI) | gaatgagttcctcgagataccattctagagggcttaaagctaccgg | 15 |

As a result, srk gene containing 1,200 bp long promoter region was separated. The amplified product was cloned into pDZTn vector pretreated with Spe I and Xho I using BD in-Fusion kit, resulting in the construction of the recombination vector pDZTn-srk. FIG. 4 shows the *Corynebacterium* chromosome insertion vector pDZTn-srk.

The patent-granted lysine production strain *Corynebacterium glutamicum* KCCM10770P was transformed with the constructed vector pDZTn-srk. After the secondary crossover, a copy of srk gene was inserted in between transposons on the chromosome. As a result, the lysine production strain *Corynebacterium glutamicum* KCCM10770P-CJ3 was prepared. To confirm the strain, PCR was performed using primer 9 and primer 16 (Table 11) facilitating the amplification of the joining region between the transposon and srk gene.

TABLE 11

| Primer | Sequence | SEQ ID. NO: |
|---|---|---|
| Tn-A-F | gctaccgctgcaccaacccc | 9 |
| Srk-1 | ataccattctagagggcttaaagctaccgg | 16 |

Example 7

Measurement of Aspartate Kinase Activity of the L-Lysine Biosynthesis Gene Multiple-Inserted Strain Aspartate kinase activity of the L-lysine production strain *Corynebacterium glutamicum* KCCM10770P-CJ2 was measured by using aspartyl hydroxamate (Pecher J-F, Capony J-P (1968) On the colorimetric determination of acyl phosphates. Anal Biochem 22: 536~539). As a result, *Corynebacterium glutamicum* KCCM10770P-CJ2 demonstrated 2.1 times higher aspartate kinase activity than the mother strain *Corynebacterium glutamicum* KCCM10770P.

TABLE 12

|  | Activity | Times |
|---|---|---|
| KCCM10770P | 26.77 | 1.00 |
| KCCM10770P-CJ2 | 56.25 | 2.10 |

Example 8

Measurement of Fructokinase Activity of the Srk Gene Inserted Strain

It was investigated whether or not fructokinase was expressed in the cells from the fructokinase expression vector and whether or not there was fructokinase activity, by the known method (Andreas Pikis et al, *Microbiology*, 148, 843-852 (2002)). *Corynebacterium glutamicum* KCCM10770P-CJ3 was cultured in LB for one day, followed by centrifugation to obtain the cells. The obtained cells were suspended in a proper buffer, followed by sonication to lysis the cells. Ultra-centrifugation was performed to obtain supernatant. The obtained supernatant was reacted with the reaction solution containing fructose, phosphoglucose, isomerase, glucose-6-phosphate dihydrogenase, ATP and NADP$^+$. The generated NADPH was quantified by measuring OD$_{340}$ with a spectrophotomer, from which fructokinase activity was indirectly calculated. The results are shown in Table 9. As shown in Table 11, *Corynebacterium glutamicum* KCCM10770P-CJ3 demonstrated the fructokinase activity at least double the activity of the mother strain *Corynebacterium glutamicum* KCCM10770P, suggesting that the fructokinase gene was expressed therein.

TABLE 13

| Test Strain | KCCM10770P | KCCM10770P-CJ3 |
|---|---|---|
| Activity[a] | 5.14 | 12.13 |

[a]nmol (generated fructose-6-phosphate) min$^{-1}$mg (protein)$^{-1}$

Example 9

Production of L-Lysine in the L-Lysine Biosynthesis Gene Multiple-Inserted Strain The L-lysine production strains *Corynebacterium glutamicum* ATCC13032-CJ1 and *Corynebacterium glutamicum* ATCC13032-CJ2 constructed in Example 5 were cultured in the following manner for the production of L-lysine.

Each of the *Corynebacterium glutamicum* mother strains ATCC13032, ATCC13032-CJ1 and ATCC13032-CJ2 was inoculated in a 250 ml corner-baffled flask containing 25 ml of the following seed medium, followed by shake-culture at 30° C. for 20 hours at 200 rpm. 1 ml of the seed culture broth was inoculated in a 250 ml corner-baffled flask containing 24 ml of the following production medium, followed by shake-culture at 30° C. for 120 hours at 200 rpm.

After completion of the culture, the production of L-lysine production was measured by HPLC. Measurement results for L-lysine in the culture broths of *Corynebacterium glutamicum* KCCM10770P and ATCC 13032, ATCC13032-CJ1 and ATCC13032-CJ2 are shown in Table 14.

TABLE 14

| Strain | Lysine (g/L) | | |
|---|---|---|---|
| | Batch 1 | Batch 2 | Batch 3 |
| ATCC13032 | 0 | 0 | 0 |
| ATCC13032-CJ1 | 4.6 | 4.5 | 4.5 |
| ATCC13032-CJ2 | 4.4 | 4.6 | 4.5 |

The L-lysine production strain *Corynebacterium glutamicum* KCCM10770P-CJ2 prepared in Example 5 was cultured as follows for the production of L-lysine.

Each of *Corynebacterium glutamicum* KCCM10770P-CJ2 and the mother strain *Corynebacterium glutamicum* KCCM10770P was inoculated in a 250 ml corner-baffled flask containing 25 ml of seed medium, followed by shake-culture at 30° C. for 20 hours at 200 rpm. 1 ml of the seed culture broth was inoculated in a 250 ml corner-baffled flask containing 24 ml of production medium, followed by shaking-culture at 30° C. for 120 hours at 200 rpm.

After completion of the culture, L-lysine production was measured by HPLC. Measurement results amounts for L-lysine in the culture broths of *Corynebacterium glutamicum* KCCM10770P and *Corynebacterium glutamicum* KCCM10770P-CJ2 are shown in Table 15.

TABLE 15

| Strain | Lysine (g/L) | | |
|---|---|---|---|
| | Batch 1 | Batch 2 | Batch 3 |
| KCCM10770P | 46.1 | 45.8 | 45.4 |
| KCCM10770P-CJ2 | 51.8 | 51.2 | 51.7 |

Seed Culture Medium (pH 7.0)
raw sugar 20 g, pepton 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium-pantothenate 2000 μg, nicotinamide 2000 μg (in distilled water 1 L)

Production Medium (pH 7.0)
glucose 100 g, $(NH_4)_2SO_4$ 40 g, soybean protein 2.5 g, corn steep solids 5 g, urea 3 g, $KH_2PO_4$ 1 g, $MgSO_4 \cdot 7H_2O$ 0.5 g, biotin 100 μg, thiamine hydrochloride 1000 μg, calcium-pantothenate 2000 μg, nicotinamide 3000 μg, $CaCO_3$ 30 g (in distilled water 1 L).

As shown in Table 15, lysine production in *Corynebacterium glutamicum* KCCM10770P-CJ2 containing the two lysine biosynthesis genes was increased by 10% compared to that in the mother strain KCCM 10770P.

Example 10

Cloning of Fluorescent Protein-Encoding gfp Gene, Construction of Recombinant Vectors (pDZTn-gfp, pDZTn300-gfp), and Development of gfp-Inserted Strain To obtain a fluorescent protein-encoding gfp gene, the nucleotide sequence information of gfp gene (NCBI accession No. SCU89686) was obtained on the basis of NIH GenBank, and based on this information, a pair of primers (Table 16, SEQ ID NOS: 37 and 38) were synthesized. PCR was performed using gfp-containing GFP Fusion TOPO® vector (Invitrogen) DNA as a template and the oligonucleotides of SEQ ID NOS: 37 and 38 as primers. The PCR was performed using PfuUltra™ high-fidelity DNA polymerase (Stratagene) for 30 cycles, each consisting of denaturation at 96° C. for 30 sec, annealing at 52° C. for 30 sec, and polymerization at 72° C. for 2 min.

TABLE 16

| Primer | Nucleotide sequence | SEQ ID NO |
|---|---|---|
| Gfp-F | atgagtaaaggagaagaactttt | 37 |
| Gfp-R | ttatttgtagagctcatccatgcc | 38 |

As a result, a 1,619-bp gfp gene containing a promoter region was obtained. The amplification product was cloned into a pDZTn vector and a pDZTn300 vector, which had been treated with the restriction enzymes SpeI and XhoI, using the BD In-Fusion kit, thereby constructing a pDZTn-gfp recombinant vector and a pDZTn300-gfp recombinant vector.

Figure 6:
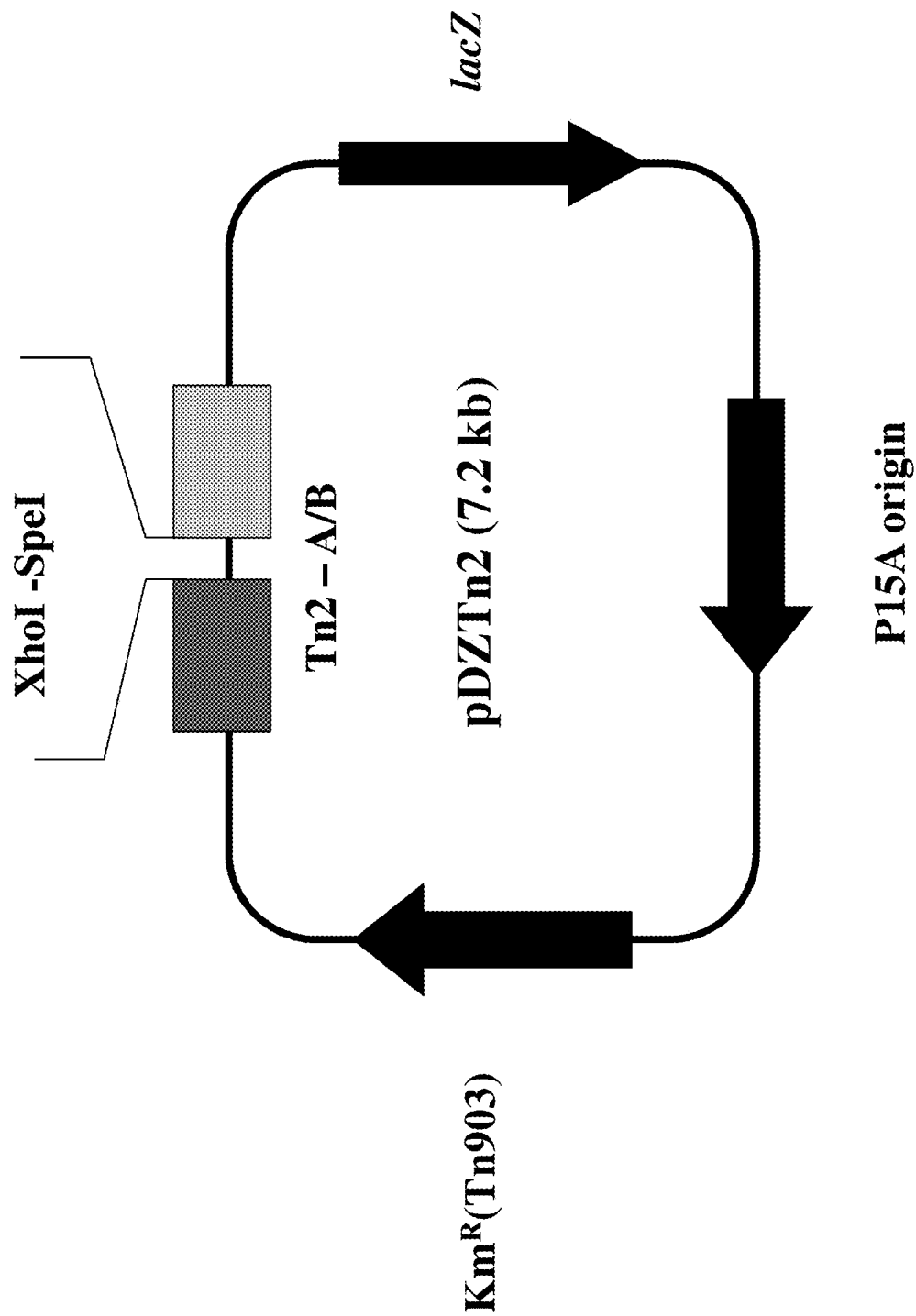
FIG. 6 shows the vector pDZTn2 for insertion into the *Corynebacterium* chromosome, in which the vector contains a restriction sites and has a partial fragment of gene encoding transposase.

FIG. 6 shows the vector pDZTn-gfp for insertion into the *Corynebacterium* chromosome.

Figure 7:
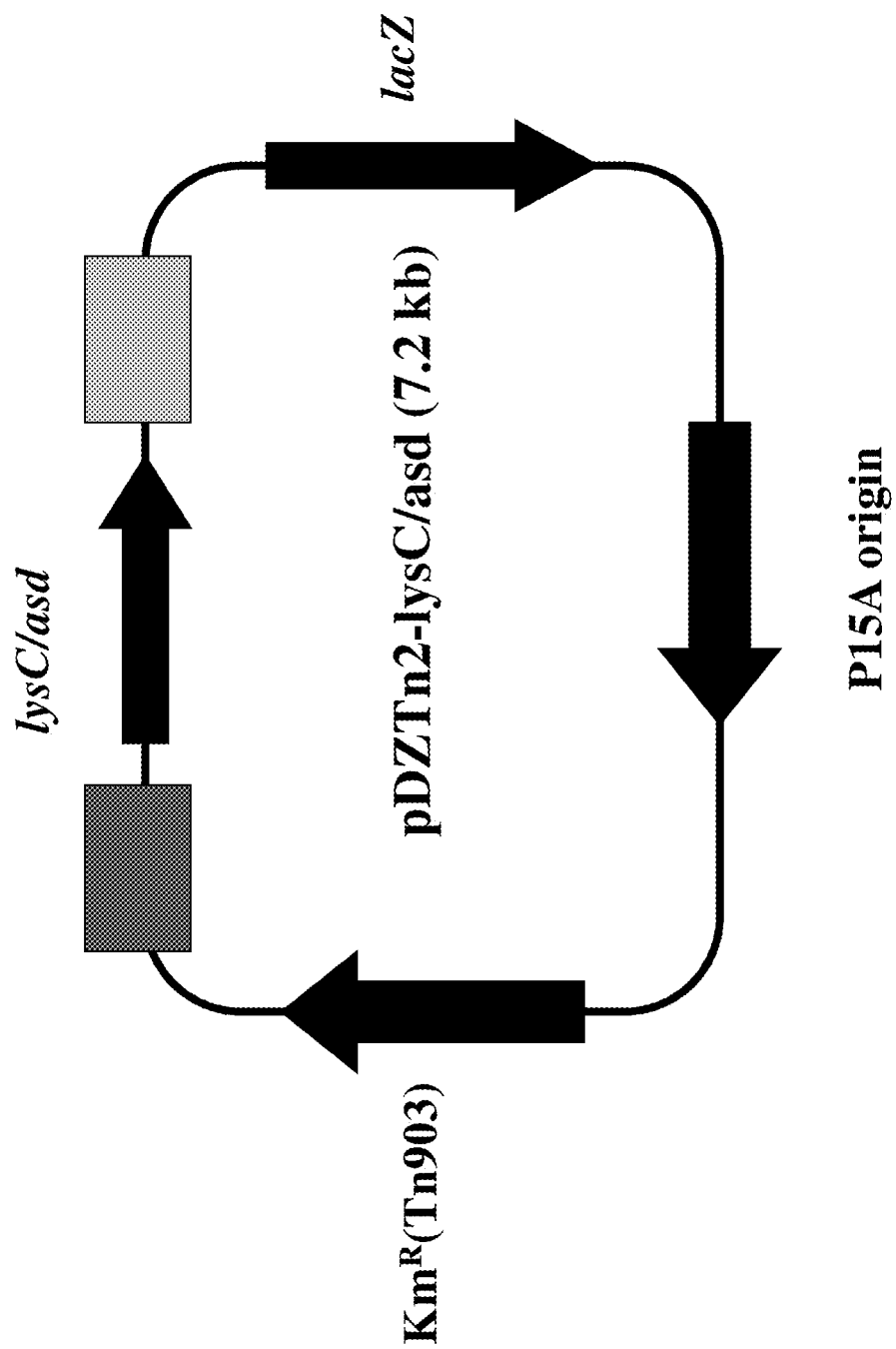
FIG. 7 shows the vector pDZTn2-lysC/asd for insertion into the *Corynebacterium* chromosome.
Figure 8:
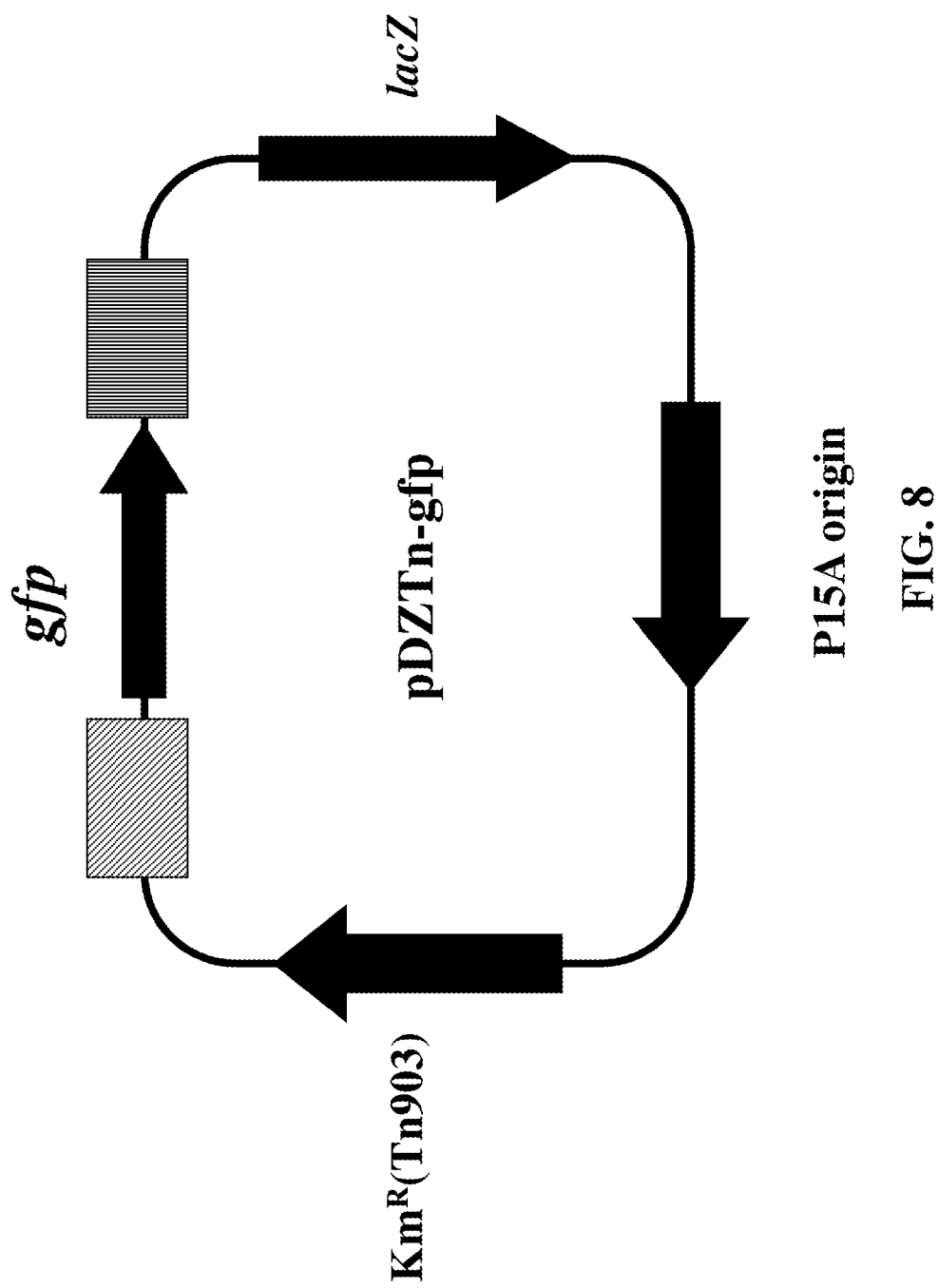
FIG. 8 shows the vector pDZTn-gfp for insertion into the *Corynebacterium* chromosome.
Figure 9:
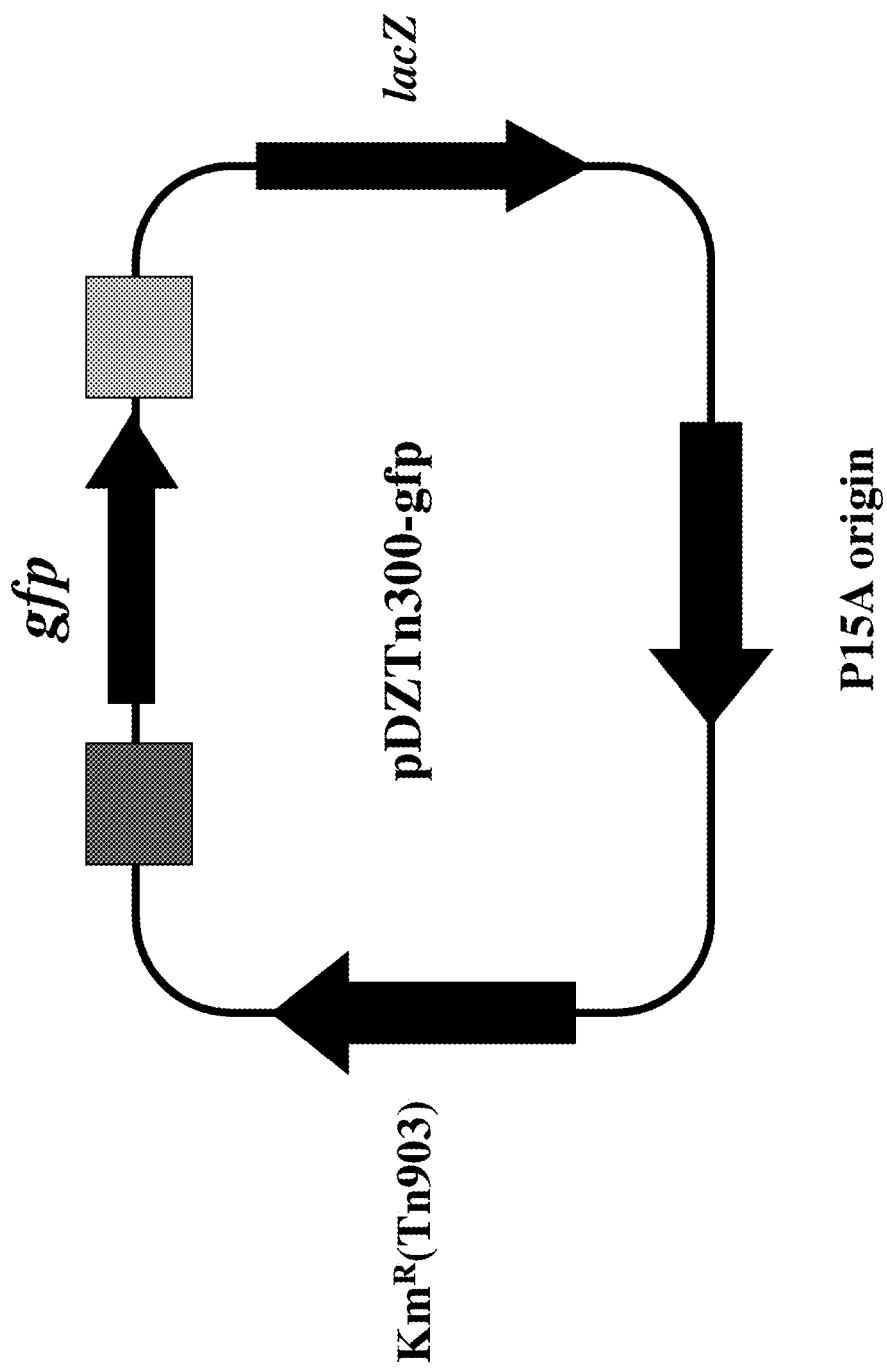
FIG. 9 shows the vector pDZTn300-gfp for insertion into the *Corynebacterium* chromosome.
Figure 10:
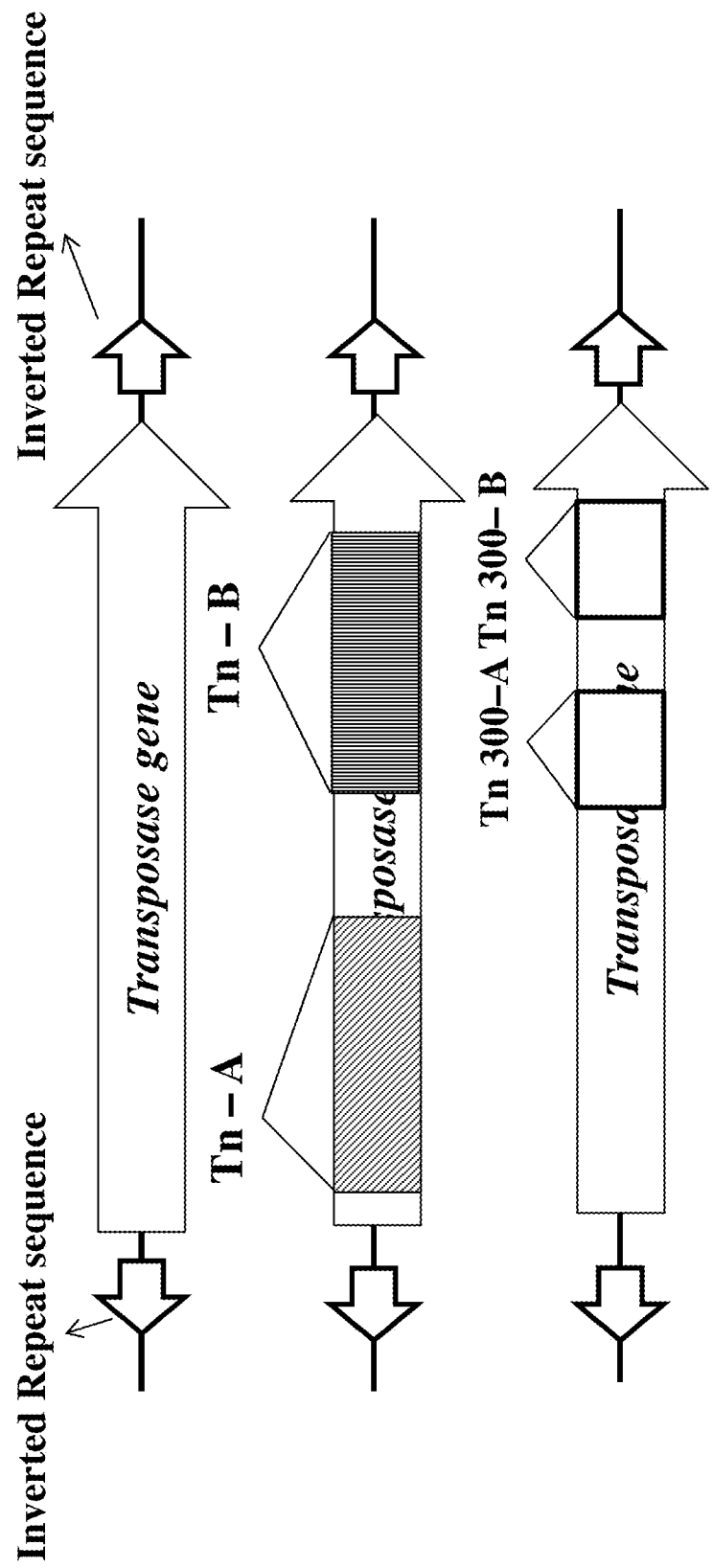
FIG. 10 shows the general structure of transposon.

FIG. 7 shows the vector pDZTn300-gfp for insertion into the *Corynebacterium* chromosome.

The constructed pDZTn-gfp vector was transformed into *Corynebacterium glutamicum*, followed by secondary crossover, thereby obtaining the transformed strain *Corynebacterium glutamicum* ATCC13032-gfp1 containing the gfp gene between the transposase genes in the chromosome. The strain was confirmed by PCR using the primers of SEQ ID NOS: 9 and 38 (Table 17) capable of amplifying a region of the transposase and gfp genes.

TABLE 17

| Primer | Nucleotide sequence | SEQ ID NO |
|---|---|---|
| OTn-A-F | gctaccgctgcaccaacccc | 9 |
| Gfp-R | ttatttgtagagctcatccatgcc | 38 |

Example 11

Development of Strain into which a Plurality of Copies of gfp were Inserted

To additionally add one or more copies of the gfp gene to the gfp-inserted strain *Corynebacterium glutamicum*

ATCC13032-gfp1 constructed in the above Example, a strain into which a plurality of copies of the gfp gene were inserted was developed in the following manner.

The above-constructed pDZTn-gfp vector was transformed into *Corynebacterium glutamicum* ATCC13032-gfp, followed by secondary crossover, thereby obtaining the transformed strain *Corynebacterium glutamicum* ATCC13032-gfp2 containing 2 copies of the gfp gene between the transposase genes in the chromosome. The strain was confirmed by PCR using the primers of SEQ ID NOS: 9 and 38 (Table 17) capable of amplifying the linkage of the transposase and gfp genes.

In order to construct a strain containing three copies of the gfp gene, the above-obtained pDZTn300-gfp was transformed into the *Corynebacterium glutamicum* ATCC13032-gfp2 strain constructed as described above, followed by secondary crossover, thereby obtaining the transformed strain ATCC13032-gfp3 containing three copies of the gfp gene. The strain was confirmed by PCR using the primers of SEQ ID NOS: 36 and 40 (Table 18) capable of amplifying a region of the transposase and gfp genes.

TABLE 18

| Primer | Nucleotide sequence | SEQ ID NO |
|---|---|---|
| Tn2-A-F | cacgcacactccatcaagtg | 36 |
| Gfp-R | ttatttgtagagctcatccatgcc | 38 |

Examples 12

Measurement of GFP Fluorescence in gfp-Inserted Strains

In order to measure GFP activity in the above-obtained transformed strains, a green fluorescence protein (GFP) enzyme method was used. The culture of the strains and the measurement of GFP activity were carried out in the following manner.

1 loop of each of the transformed *Corynebacterium glutamicum* strains was inoculated in a 250-ml flask containing 25 ml of LB medium and was shake-cultured at 32° C. and 200 rpm until the optical density (OD) reached 10-15. After completion of the culture, the cells were collected by centrifugation, suspended in 100 mM Tris-Hcl buffer (pH 7.0), disrupted by sonication, and then subjected high-speed centrifugation to obtain a supernatant containing a cell extract. The amount of protein in the supernatant was measured by Bradford analysis. Then, the same amount of the cell extract was irradiated with light at an excitation wavelength of 488 nm using the method of Laure Gory et al. (FEMS Microbiology Letters 194, 127-133, 2001), and light at an emission wavelength of 511 nm was measured using the LS-50B spectrophotometer (Perkin-Elmer), thereby determining the expression of the GFP gene. Table 19 below shows the results of measuring GFP activity in each of the strains.

TABLE 19

| Strain | Fluorescence/mg | | |
|---|---|---|---|
| | Batch 1 | Batch 2 | Batch 3 |
| ATCC13032 | 0 | 0 | 0 |
| ATCC13032-gfp1 | 153 | 183 | 165 |

TABLE 19-continued

| Strain | Fluorescence/mg | | |
|---|---|---|---|
| | Batch 1 | Batch 2 | Batch 3 |
| ATCC13032-gfp2 | 295 | 307 | 315 |
| ATCC13032-gfp3 | 467 | 523 | 536 |

As a result, it was shown that the intensity of fluorescence increased in proportion to the copy number of gfp. This suggests that the desired copy number of gfp was inserted into the chromosome of each strain.

Example 13

Evaluation of Genetic Stability of Strain by Subculture

Transposon is known as a mechanism for the survival of microorganisms under extreme conditions or a mechanism for the evolution of microorganisms during continuous culture for a long time. When a target gene is inserted into the transposase gene, the transposase gene is inactivated, and thus the stability of the inserted gene increases. In this Example, the genetic stability of the inserted gene was evaluated in the following manner.

The above-obtained transformed strain ATCC13032-gfp1 is a strain in which one of three transposase genes was inactivated, and the transformed strain ATCC13032-gfp3 is a strain in which all the three transposase genes were inactivated. Each of the strains ATCC13032-gfp1 and ATCC13032-gfp3 was cultured on solid medium at 32° C. for 3 days, and then inoculated and cultured on fresh solid medium for 3 days under the same conditions. This culture process was repeated for 6 months. After 6 months, 1 loop of each of the strains, which were about 60 times subcultured, was inoculated in a 250-ml flask containing 25 ml of LB medium and was shake-cultured at 32° C. at 200 rpm until the optical density (OD) reached 10-15. After completion of the culture, the cells were collected by centrifugation and measured for gfp according to the above-described method. As a result, in the ATCC13032-gfp1 strain in which transposases remain, the gfp activity increased about 1.5 times at 6 months after subculture compared to that in the non-cultured strain, but in the ATCC13032-gfp3 in which all the transposases were inactivated, the gfp activity was the same as that in the non-cultured strain (Table 20). Thus, it can be seen that the copy number of the gfp gene in the ATCC13032-gfp1 strain increased due to the activation of transposases under subculture conditions, whereas the copy number of the gfp gene in the ATCC13032-gfp3 strain in which all transposases had been inactivated did not increase, suggesting that the genetic stability of the ATCC13032-gfp3 strain is more excellent than that of ATCC13032-gfp1 strain.

TABLE 20

| Strain | Fluorescence/mg | | |
|---|---|---|---|
| | Batch 1 | Batch 2 | Batch 3 |
| ATCC13032-gfp1 (before culture) | 155 | 164 | 153 |
| ATCC13032-gfp1 (after subculture) | 231 | 253 | 255 |

TABLE 20-continued

| | Fluorescence/mg | | |
|---|---|---|---|
| Strain | Batch 1 | Batch 2 | Batch 3 |
| ATCC13032-gfp3 (before culture) | 465 | 515 | 524 |
| ATCC13032-gfp3 (after subculture) | 478 | 523 | 517 |

What is claimed is:

1. A method of inactivating a transposase in the chromosome of a *Corynebacterium* sp. microorganism and expressing a target gene in the *Corynebacterium* sp. microorganism, the method comprising the steps of:
   1) introducing the target gene into a gene encoding the transposase in the chromosome of the *Corynebacterium* sp. microorganism to transform the *Corynebacterium* sp. microorganism; and
   2) culturing the transformed microorganism,
wherein the target gene is introduced using a transformation vector in which the target gene is inserted in between a 5' terminal fragment and a 3' terminal fragment of a gene encoding a transposase derived from the *Corynebacterium* sp.

2. The method of claim 1, wherein the target gene is introduced into the gene encoding the transposase.

3. The method of claim 1, wherein the transposase is an ISCg1 type or ISCg2 type transposase.

4. The method of claim 3, wherein a nucleic acid sequence encoding the ISCg1 type transposase is represented by SEQ ID NO: 22, and a nucleic acid sequence encoding the ISCg2 type transposase is represented by SEQ ID NO: 29.

* * * * *